United States Patent
Hayes

(10) Patent No.: US 12,178,583 B2
(45) Date of Patent: Dec. 31, 2024

(54) BASKET-TYPE EP CATHETER WITH ELECTRODE POLLING FOR SEQUENTIAL ELECTRODE SAMPLING

(71) Applicant: Lake Region Manufacturing, Inc., Chaska, MN (US)

(72) Inventor: John Michael Hayes, Cork (IE)

(73) Assignee: Lake Region Manufacturing, Inc., Chaska, MN (US)

(*) Notice: Subject to any disclaimer, the term of this patent is extended or adjusted under 35 U.S.C. 154(b) by 645 days.

(21) Appl. No.: 16/894,238

(22) Filed: Jun. 5, 2020

(65) Prior Publication Data

US 2020/0383599 A1 Dec. 10, 2020

Related U.S. Application Data

(60) Provisional application No. 62/858,375, filed on Jun. 7, 2019.

(51) Int. Cl.
| | |
|---|---|
| A61B 5/301 | (2021.01) |
| A61B 5/00 | (2006.01) |
| A61B 5/287 | (2021.01) |

(52) U.S. Cl.
CPC ............ *A61B 5/301* (2021.01); *A61B 5/287* (2021.01); *A61B 5/6858* (2013.01); *A61B 2562/0209* (2013.01)

(58) Field of Classification Search
None
See application file for complete search history.

(56) References Cited

U.S. PATENT DOCUMENTS

| | | | |
|---|---|---|---|
| 5,313,943 A | 5/1994 | Houser et al. | |
| 5,626,619 A * | 5/1997 | Jacobson | A61N 1/3931 607/7 |
| 5,647,870 A * | 7/1997 | Kordis | A61B 5/6858 606/41 |
| 8,335,551 B2 | 12/2012 | Lee et al. | |

(Continued)

FOREIGN PATENT DOCUMENTS

| | | |
|---|---|---|
| WO | WO 94/07412 | 4/1994 |
| WO | WO2019/079378 A1 | 4/2019 |

OTHER PUBLICATIONS

"European Search Report, Application No. 20178846.0 Dated Nov. 4, 2020."

*Primary Examiner* — Sean W Collins
*Assistant Examiner* — Nora W Rhodes
(74) *Attorney, Agent, or Firm* — Michael F. Scalise

(57) ABSTRACT

A basket-type EP catheter is described. The EP catheter comprises a catheter proximal end that is electrically connected to a controller by an electrical cable having a single voltage-out (Vout) conductor and a catheter distal end supporting a distal connector that is detachably connectable to a basket-shaped configuration of a plurality of splines. Each spline supports an array of electrodes. By sampling the voltage signal on each of the plurality of electrodes sequentially or consecutively, only one Vout conductor is needed to transmit the voltage sample to the controller. In comparison to conventional EP catheters, this greatly reduces the number of conductors extending along the catheter shaft. The use of a Vout conductor is implemented by connecting a polling circuit or a "one-shot" circuit and a signal pass-transistor or transmission gate to each electrode.

39 Claims, 15 Drawing Sheets

(56) References Cited

U.S. PATENT DOCUMENTS

| | | |
|---|---|---|
| 8,406,898 B2 | 3/2013 | Wulfman |
| 8,412,347 B2 | 4/2013 | Zdeblick |
| 8,473,069 B2 | 6/2013 | Bi et al. |
| 8,655,427 B1 | 2/2014 | Greenspan et al. |
| 9,179,971 B2 | 11/2015 | Kirschenman |
| 9,987,083 B2 | 6/2018 | Gelbart et al. |
| 10,076,258 B2 | 9/2018 | Thakur et al. |
| 11,559,349 B2 * | 1/2023 | Bar-Tal .............. A61B 18/1492 |
| 2002/0198522 A1 | 12/2002 | Kordis |
| 2010/0204766 A1 | 8/2010 | Zdeblick et al. |
| 2010/0261994 A1 * | 10/2010 | Davalos ............. A61B 18/1477 600/407 |
| 2012/0253161 A1 | 10/2012 | Harlev et al. |
| 2012/0271135 A1 | 10/2012 | Burke |
| 2015/0065836 A1 | 3/2015 | Thakur et al. |
| 2015/0351652 A1 * | 12/2015 | Marecki ............. A61B 18/1492 29/829 |
| 2018/0256248 A1 | 9/2018 | Bae et al. |
| 2018/0325455 A1 | 11/2018 | Ellason |
| 2019/0030328 A1 * | 1/2019 | Stewart ............. A61B 18/1492 |
| 2019/0117113 A1 * | 4/2019 | Curran ................ A61B 5/0538 |

* cited by examiner

BASKET-TYPE EP CATHETER WITH ELECTRODE POLLING FOR SEQUENTIAL ELECTRODE SAMPLING

CROSS-REFERENCE TO RELATED APPLICATION

This application claims priority to U.S. Provisional Application Ser. No. 62/858,375, filed on Jun. 7, 2019.

BACKGROUND OF THE INVENTION

1. Field of the Invention

The present invention relates to the field of medical devices. More specifically, the present invention is directed to determining and representing anatomical and physiological information related to a heart using a contact catheter.

2. Prior Art

The human heart routinely experiences electrical impulses traversing its many surfaces and ventricles, including the left atrium. Just prior to each heart contraction, the heart depolarizes and repolarizes as electrical currents spread across the heart and throughout the body. In healthy hearts, the surfaces and ventricles of the heart experience an orderly progression of depolarization waves. In unhealthy hearts, such as those experiencing atrial arrhythmia, including for example, ectopic atrial tachycardia, atrial fibrillation, and atrial flutter, the progression of the depolarization wave becomes chaotic. Arrhythmias may persist because of scar tissue or other obstacles to rapid and uniform depolarization. These obstacles may cause depolarization waves to electrically circulate through some parts of the heart more than once. Atrial arrhythmia can create a variety of dangerous conditions, including irregular heart rates, loss of synchronous atrioventricular contractions, and blood flow stasis. These conditions are associated with a variety of ailments, including death.

Catheters are used in a variety of diagnostic and therapeutic medical procedures to diagnose and correct conditions such as atrial arrhythmia, including for example, ectopic atrial tachycardia, atrial fibrillation, and atrial flutter. Typically, in such a procedure, a catheter carrying one or more electrodes is moved through a patient's vasculature to the heart under fluoroscopy-guided observation. The electrodes may be used for mapping, ablation, diagnosis, or other treatments.

When an ablation therapy is desired to alleviate symptoms including atrial arrhythmia, the ablation catheter imparts ablative energy to cardiac tissue to create a lesion in the cardiac tissue. The lesioned tissue is less capable of conducting electrical signals, thereby disrupting undesirable electrical pathways and limiting or preventing stray electrical signals that lead to arrhythmias. The ablation catheter may utilize ablative energy including, for example, radiofrequency (RF), cryoablation, laser, chemical, and high-intensity focused ultrasound.

However, before a physician can perform an ablation therapy, the anatomical structure and physiological health of the heart must first be obtained. This is typically done using a contact catheter. In contact mapping, a catheter is advanced into the heart and, after determining that a distal electrode-carrying spline section of the catheter is in stable and steady contact with the endocardium surface of a heart chamber of interest, physiological signals resulting from electrical activity of the heart are acquired from one or more electrodes supported on the splines. Electrical activity is usually measured sequentially on a point-by-point basis at about 50 to 200 locations on the endocardium surface of the heart to construct an electro-anatomical depiction of the heart. The generated map then serves as the basis for deciding on a therapeutic course of action, for example, tissue ablation, to alter the propagation of the heart's electrical activity and to restore normal heart rhythm.

While conventional basket-type EP (electro-physiology) catheters have many electrodes, for example eight electrodes on eight splines for a total of 64 electrodes or 16 electrodes on eight splines for a total of 128 electrodes, to sufficiently map the anatomical structure of the heart, they require a separate voltage-out (Vout) conductor for each electrode. The Vout conductors bring the electrode sample signal down the catheter to the proximal connector detachably connected to a controller for signal analysis. Not only is having a dedicated Vout conductor for each electrode in a spline system complicated and difficult to construct, it does not much leave room in the catheter shaft for other structure, such as a delivery lumen, a suction lumen, a fiber optic cable, pull wires, and the like.

Therefore, there is a need for an improved basket-type EP catheter that is useful for mapping the anatomical structure and physiological health of the heart prior to a physician performing a diagnostic or therapeutic medical procedure. The improved basket-type EP catheter of the present invention satisfies this need by providing one Vout conductor system connecting from the proximal end of the catheter to the distal basket-shaped electrode-carrying spline system. Only one Vout conductor is needed because the individual electrodes of the spline system are sampled sequentially by using a "one-shot" circuit and a signal pass-transistor or transmission gate at each electrode. The use of one Vout conductor provides ample space for other structure that is desirable in catheters, such as the previously described delivery lumen, suction lumen, fiber optic cable, pull wires, and the like. In the alternative, since only one Vout conductor connects from the proximal end of the catheter to the distal basket-shaped electrode-carrying spline system, the EP catheter of the present invention has a smaller diameter or French size than conventional EP catheters. This means the basket-type EP catheter of the present invention is less obstructive than conventional mapping catheters as it is navigated through the patient's vasculature to the heart.

SUMMARY OF THE INVENTION

By sampling the voltage signal on each of a plurality of electrodes sequentially or consecutively, only one Vout conductor system is needed to transmit the voltage sample from each electrode to the proximal connector and then to the controller. This greatly reduces the number of conductors extending along the catheter shaft, which means there is ample room for other structure or lumens that may be useful to a physician during a mapping procedure. The use of a single Vout conductor system is implemented by connecting a "one-shot" circuit and a signal pass-transistor or transmission gate to each electrode. For example, if there are 128 electrodes spaced along four splines, a sample frequency of 128 KHz is sufficient to sample every electrode every millisecond. Consequently, the use of a single Vout conductor system to sequentially sample the voltage signal from each of a plurality of electrodes is an advancement over known basket-type EP catheters.

Thus, one embodiment of the present EP catheter comprises a catheter system, comprising a controller, a catheter extending from a catheter proximal end to a catheter distal end. The catheter comprises a catheter proximal connector at the catheter proximal end, the catheter proximal connector being electrically connectable to the controller, a catheter distal connector supported at the catheter distal end, and an electrical cable comprising a catheter clock/trigger (Clk/Trig) conductor, a catheter ground (Gnd) conductor, a catheter voltage-source (Vsource) conductor, and a catheter voltage-out (Vout) conductor. The electrical cable extends along the catheter to the catheter proximal and distal catheter connectors. At least a first spline extends from a spline proximal anchor electrically connected to the electrical cable at the catheter distal connector to a spline distal anchor. At least three electrodes are supported by the first spline, the three electrodes comprising a first spline first electrode located closest to the spline proximal anchor, a first spline second electrode, and a first spline third electrode located furthest from the spline proximal anchor. Then, with the catheter proximal connector electrically connected to the controller through the electrical cable, the controller is configured to initiate a first consecutive electrode sampling sequence along the first spline by sending a clock/trigger (Clk/Trig) signal along the catheter Clk/Trig conductor to a first Clk/Trig conductor connected to a first spline first polling circuit configured to activate the first spline first electrode and then pass a first spline first electrode voltage sample to the catheter Vout conductor electrically connected to the controller. After the first spline first electrode voltage sample has been sent to the controller, the first spline first polling circuit is configured to send a Clk/Trig signal along a second Clk/Trig conductor connected to a first spline second polling circuit configured to activate the first spline second electrode and then pass a first spline second electrode voltage sample to the catheter Vout conductor electrically connected to the controller. And, after the first spline second electrode voltage sample has been sent to the controller, the first spline second polling circuit is configured to send a Clk/Trig signal along a third Clk/Trig conductor connected to a first spline third polling circuit configured to activate the first spline third electrode and then pass a first spline third electrode voltage sample to the catheter Vout conductor electrically connected to the controller. Then, after the first spline third electrode voltage sample has been sent to the controller, the controller is configured to initiate a second consecutive electrode sampling sequence.

Another embodiment of the present EP catheter comprises a controller, a catheter extending from a catheter proximal end to a catheter distal end. The catheter comprises a catheter proximal connector at the catheter proximal end, the catheter proximal connector being electrically connectable to the controller, a catheter distal connector supported at the catheter distal end, and an electrical cable comprising a clock/trigger (Clk/Trig) conductor, a ground (Gnd) conductor, a voltage-source (Vsource) conductor, and a voltage-out (Vout) conductor, wherein the electrical cable extends along the catheter to the catheter proximal and distal catheter connectors. At least a first spline extends from a spline proximal anchor electrically connected to the electrical cable at the catheter distal connector to a spline distal anchor. At least three electrodes are supported by the first spline, the three electrodes comprising a first spline first electrode, a first spline second electrode, and a first spline third electrode. Then, with the catheter proximal connector electrically connected to the controller through the electrical cable, the controller is configured to initiate a first consecutive electrode sampling sequence along the first spline by sending a clock/trigger (Clk/Trig) signal along the catheter Clk/Trig conductor to a first Clk/Trig conductor connected to a first spline first polling circuit configured to activate the first spline first electrode and then pass a first spline first electrode voltage sample to the catheter Vout conductor electrically connected to the controller. After the first spline first electrode voltage sample has been sent to the controller, the first spline first polling circuit is configured to send a Clk/Trig signal along a second Clk/Trig conductor connected to a first spline second polling circuit configured to activate the first spline second electrode and then pass a first spline second electrode voltage sample along the catheter Vout to the controller. And, after the first spline second electrode voltage sample has been sent to the controller, the first spline second polling circuit is configured to send a Clk/Trig signal along third Clk/Trig conductor connected to a first spline third polling circuit configured to activate the first spline third electrode and then pass a first spline third electrode voltage sample along the catheter Vout conductor to the controller. Then, after the first spline third electrode voltage sample has been sent to the controller, the controller is configured to initiate a second consecutive electrode sampling sequence.

These and other aspects of the present invention will become increasingly more apparent to those skilled in the art by reference to the following detailed description and to the appended drawings.

DETAILED DESCRIPTION OF THE PREFERRED EMBODIMENTS

As used herein, the terms "sampling sequence", "consecutive electrode sampling sequence" and "consecutively sampling" mean that the electrodes on a spline or a number of splines forming a spline system are sampled in a consecutive manner with a second or next electrode being sampled following sampling of a first electrode or an electrode located immediately before the second electrode without interruption.

Commercially available basket-type EP catheters have many electrodes. For example, there are basket-type EP catheters that have eight electrodes on eight splines for a total of 64 electrodes or 16 electrodes on eight splines for a total of 128 electrodes. Conventional systems require a separate voltage-out (Vout) conductor for each electrode. The dedicated Vout conductor passes voltage from an electrode to signal analysis hardware connected to the proximal end of the catheter. This means that there is a separate Vout conductor connected to each electrode of a spline and each spline Vout conductor is in turn connected to a respective catheter Vout conductor extending to a proximal connector that is connected to the signal analysis hardware, for example a controller.

According to the present invention, elimination of separate Vout conductors for each electrode supported by a spline is implemented by connecting a "one-shot circuit" and a signal pass-transistor or transmission gate to each electrode in a spline so that electrical signals are transmitted consecutively one-by-one from a plurality of electrodes along a single Vout conductor system to the proximal connector 14. For example, in a spline system having 128 electrodes, by using a sample frequency of 128 KHz, each electrode of the plurality of electrodes is sampled every millisecond, which is sufficient to track the signal of each electrode along a single Vout conductor.

In that manner, the present invention greatly reduces the number of electrical conductors that are needed for a spline system having many electrodes, for example the exemplary 64 or 128 electrode systems discussed above. By sampling the electrical signal from each electrode consecutively, only one Vout conductor is required in the catheter and in each of a plurality of splines comprising a spline system. As will be described in greater detail hereinafter, the catheter comprises a clock/trigger (Clk/Trig) conductor, a ground (Gnd) conductor, a voltage-source (Vsource) conductor and a voltage-out (Vout) conductor. There are corresponding Clk/Trig, Gnd, Vsource and Vout conductors in each spline. The catheter Vout conductor and the Vout conductors in each spline make up the so-called "Vout conductor system". It is the Clk/Trig conductor that is connected to the "one-shot circuit" and the signal pass-transistor or transmission gate.

Figure 1:
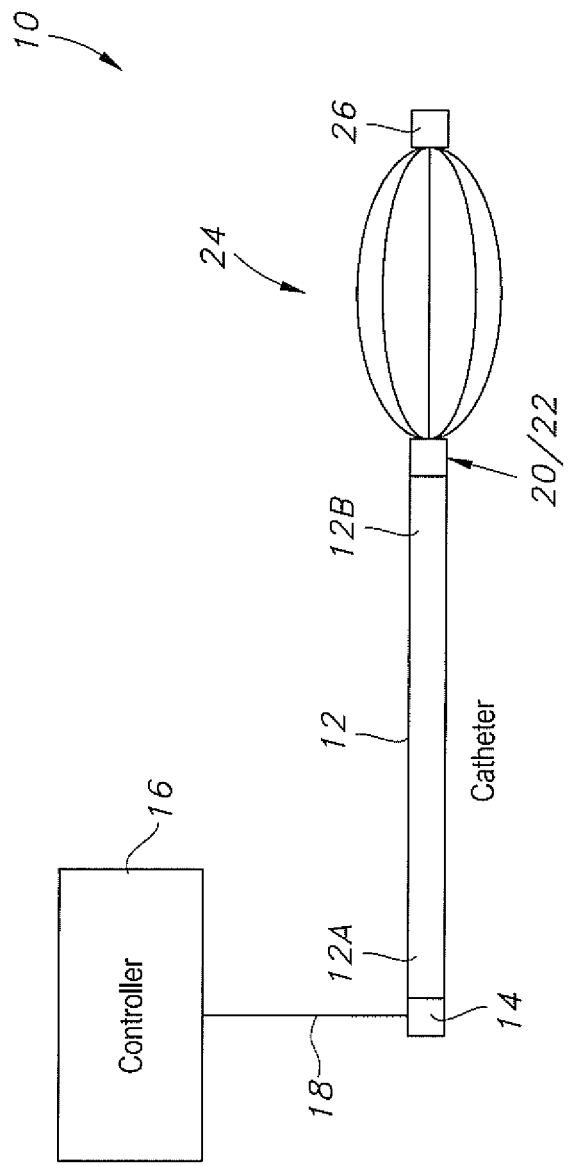
FIG. 1 is a schematic of a basket-type EP catheter system 10 according to the present invention.

Turning now to the drawings, FIG. 1 illustrates a basket-type EP (electro-physiology) catheter system 10 according to the present invention. The catheter system 10 generally comprises a catheter 12 extending from a catheter proximal end 12A to a catheter distal end 12B. The catheter proximal end 12A has a proximal connector 14 which is electrically connected to a controller 16 by a controller cable 18. The catheter distal end 12B supports a distal connector 20 (FIGS. 4A and 4B) which, as will be described in detail hereinafter, detachably connects to the proximal anchor 22 (FIGS. 2 and 5) of a basket-shaped configuration of a plurality of splines 24. Each spline 24 of the basket-shaped configuration supports an array of electrodes (not shown in FIG. 1). The splines 24 extend distally from the proximal anchor 22 to a terminal anchor 26 (FIG. 1). While a plurality of splines 24 are shown in the drawing, the broadest form of the present invention has a single spline 24 extending from the proximal anchor 22 to the terminal anchor 26.

An exemplary catheter 12 is a tubular member that extends from the proximal connector 14 at the catheter proximal end 12A to the distal connector 20 at the catheter distal end 12B. The tubular catheter 12 is formed of a polymeric material, such as of PEBAX, encasing a tubular wire braided as a mesh. A liner of a second polymeric material, for example PTFE, resides inside the PEBAX tube. In some embodiments, the catheter 12 has a delivery lumen (not shown) and the PTFE liner provides the delivery lumen with sufficient lubricity so that medical instruments, devices, and the like, slide through the lumen with a minimal amount of force. The delivery lumen is sized and shaped to receive, for example, instruments, fluids, media, and the like.

Figure 2:
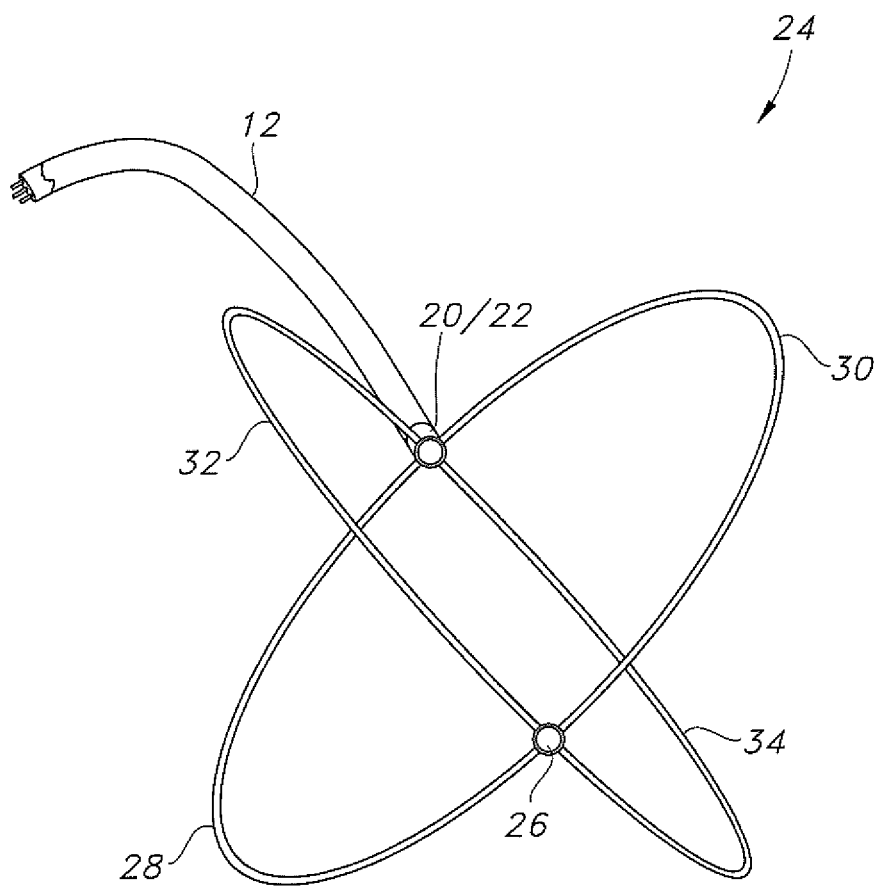
FIG. 2 is a perspective view of the catheter 12 connected to the spline system 24 for the exemplary basket-type EP catheter system 10 according to the present invention.

FIG. 2 is a perspective view of the exemplary basket-type EP catheter 12 connected to the spline system 24 of the present invention. The distal connector 20 of the catheter 12 is configured for detachably connecting to the proximal anchor 22 of the exemplary basket-shaped spline system 24 comprising four splines 28, 30, 32 and 34. The distal or terminal anchor 26 secures the splines 28 to 34 in place. As those skilled in the art will readily appreciate, other spline systems having less than four splines, for example one, two or three splines, and more than four splines, for example five splines, six splines, eight splines and more are within the scope of the present invention.

Figure 3A:
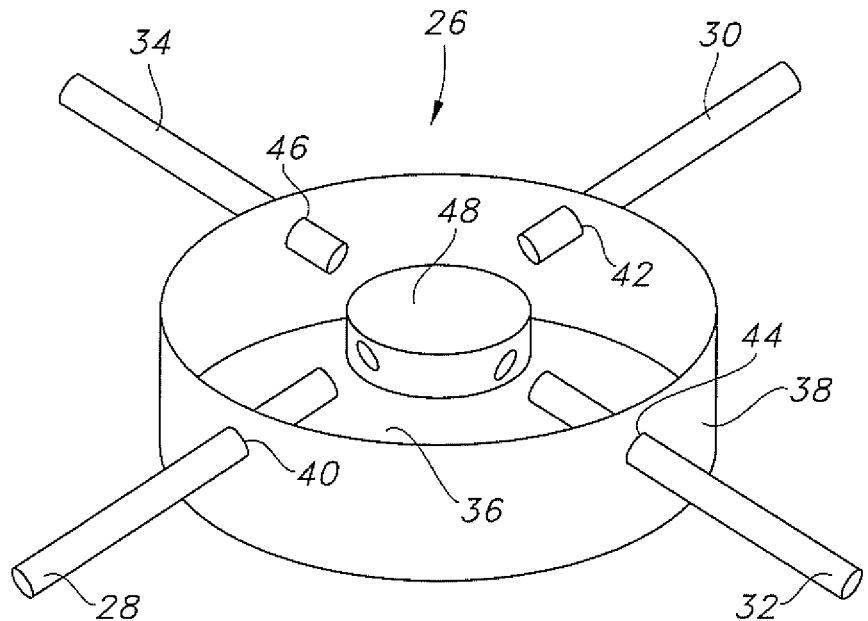
FIG. 3A is a perspective view of the four-spline system shown in FIG. 2 with splines 28, 30, 32 and 34 being connected to a terminal anchor 26.
Figure 3B:
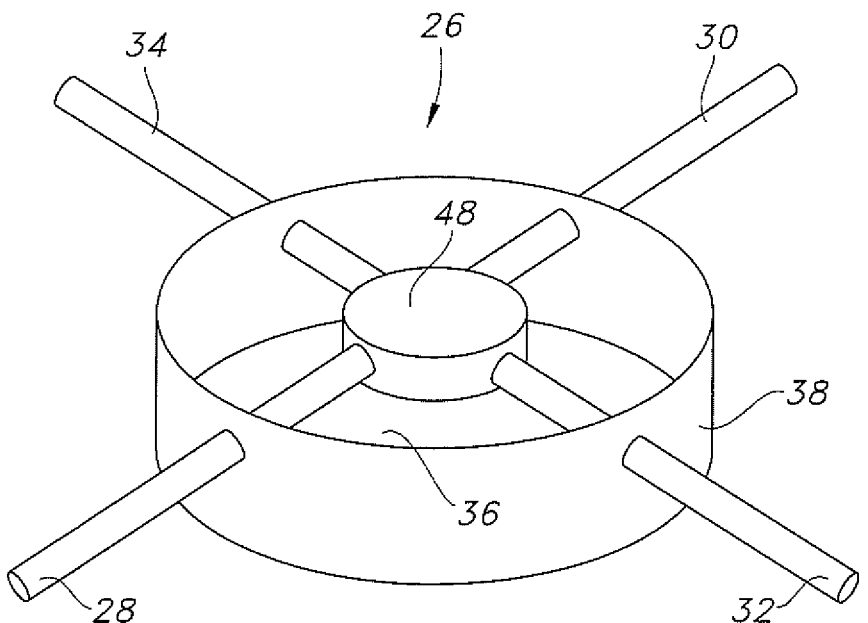
FIG. 3B is a perspective view of the splines 28, 30, 32 and 34 of the spline system 24 shown in FIG. 3A connected to the terminal anchor 26.

FIGS. 3A and 3B illustrate an exemplary embodiment of a terminal anchor 26 for the four-spline system 24 shown in FIG. 2. The terminal anchor 26 is comprised of a terminal plate 36 supporting an annular wall 38 extending proximally from a peripheral edge of the plate. The annular wall 38 is provided with four openings 40, 42, 44 and 46 spaced at 90° intervals about the circumference thereof. The four splines 28, 30, 32 and 34 shown in FIG. 2 extend through respective ones of the openings 40, 42, 44 and 46 to connect to a terminal connector 48 of the anchor 26. In addition to anchoring the splines in place, the terminal connector 48 electrically connects the distal end of the first spline 28 to the distal end of the second spline 30 and the distal end of the third spline 32 to the distal end of the fourth spline 34 while the annular wall 42 maintains the splines in an evenly spaced-apart relationship. FIG. 3A shows the distal end of the splines 28 to 34 being moved through the openings 40 to 46 in the annular wall 38 but before they are electrically connected to the terminal connector 48. FIG. 3B shows the splines 28 to 40 anchored in place in the terminal connector 48.

Figure 3C:
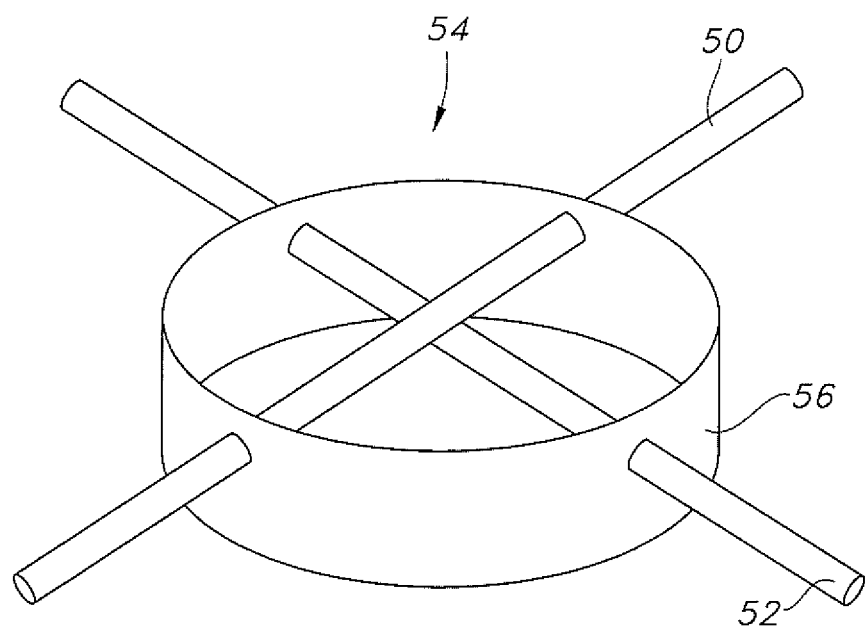
FIG. 3C is a perspective view of a two-spline system with splines 50 and 52 supported by a terminal anchor 54.

FIG. 3C illustrates an alternate embodiment of a spline system according to the present invention. This embodiment comprises two splines 50 and 52 that extend from the proximal anchor 22 shown in FIGS. 1 and 2 to a terminal anchor 54. Terminal anchor 54 differs from the terminal anchor 26 shown in FIGS. 3A and 3B in that it does not have the terminal connector 48. Instead, each of the splines 50 and 52 pass into an opening in the annular wall 56 of the terminal anchor 54 and out through a diametrically opposed opening to then extend back to the proximal anchor 22.

Figure 4:
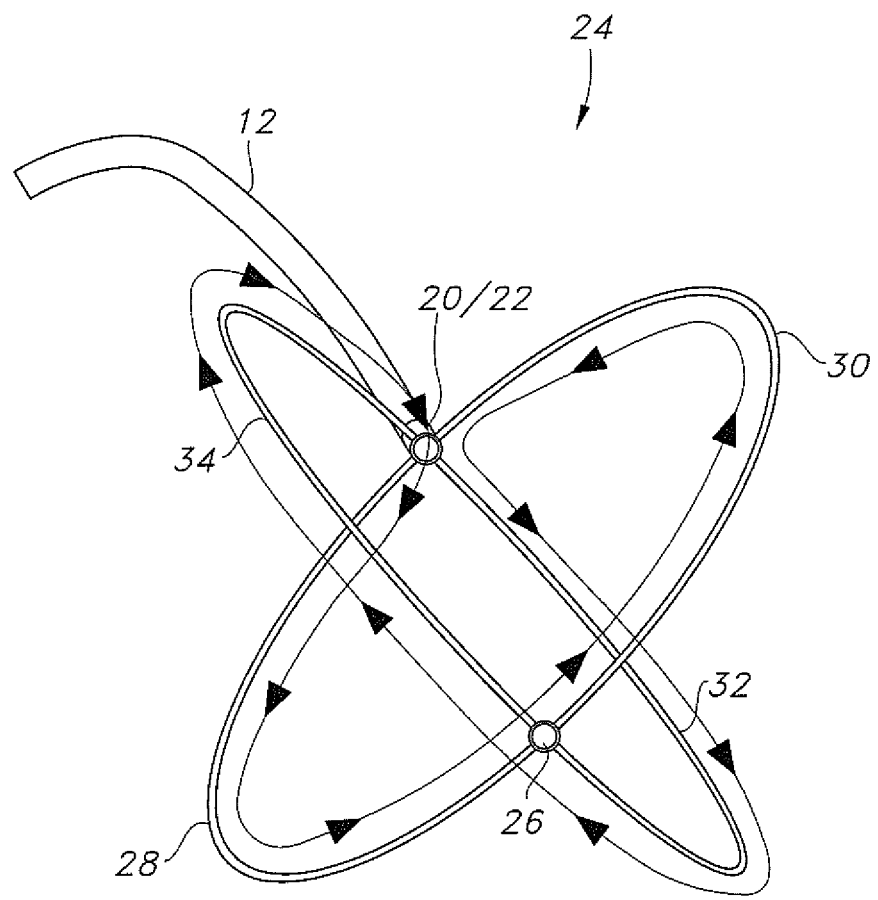
FIG. 4 is a perspective view of a consecutive sampling sequence for the spline system 24 shown in FIG. 2.

FIG. 4 shows a consecutive sampling sequence for the exemplary catheter 12 shown in FIG. 2. The spline system 24 can be either that shown in FIGS. 3A and 3B or in FIG. 3C. The controller 16 (FIG. 1) initiates a sampling trigger signal that initiates sampling of the voltage on the proximal-most electrode closest to the proximal anchor 22 on the first spline 28, followed by the next most proximal electrode until all the electrodes on spline 28 have been sampled. The sampling trigger signal then moves through the distal anchor 26 and triggers sampling of the distal-most electrode on the second spline 30. This is followed by sampling the next most distal electrode on the second spline and continuing until all the electrodes on that spline 30 have been sampled. The sampling trigger signal then moves through the proximal anchor 22 to consecutively sample the proximal-most electrode on the third spline 38, followed by sampling the next most proximal electrode until all the electrodes on the third spline have been sampled. The sampling trigger signal then moves through the distal anchor 26 and samples the distal-most electrode on the fourth spline 34. This is followed by sampling the next most distal electrode on the fourth spline and continuing until all the electrodes on the fourth spline 34 have been sampled. This completes one sampling sequence. At this stage the controller 16 is timed to emit a second trigger signal and thereby initiate another sampling sequence beginning again with the proximal-most electrode on the first spline 28 and stepping through the second, third and fourth splines 30, 32 and 34 in order. For a spline system of less than four splines, for example two or three splines, or more than four splines, for example five, six, seven, eight, or more splines, the same sampling sequence applies.

Figure 5:
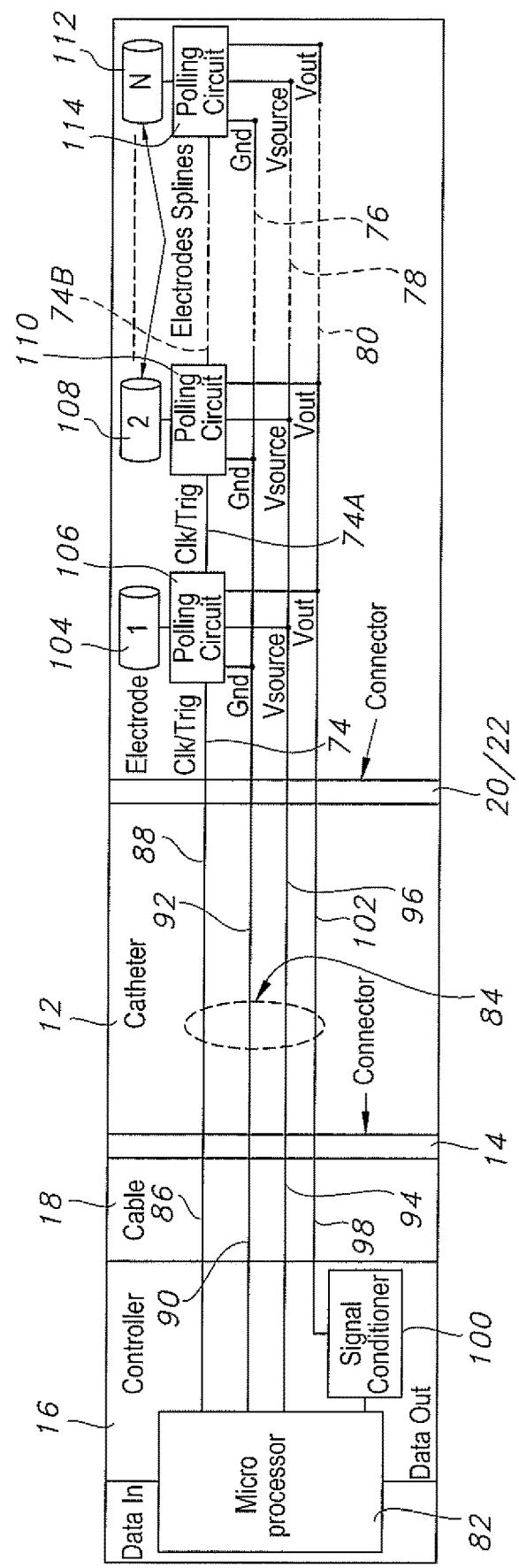
FIG. 5 is a schematic drawing of a simplified form of a consecutive sampling sequence produced by the basket-type EP catheter system 10 according to the present invention.

FIG. 5 is a schematic drawing showing the sampling sequence of the present invention in a simplified form. The controller cable 18 carrying conductors 86, 90, 94 and 98 connects from the controller 16 to the proximal connector 14. The proximal connector provides for detachably connecting the controller cable 18 to a catheter cable 84 that extends the length of the catheter 12 to the distal connector 20. The catheter cable 84 supports conductors 88, 92, 96 and 102. The distal connector 20 provides for detachably connecting the catheter cable 84 to the proximal anchor 22 of the spline system 24 (FIGS. 1 and 2).

The controller cable 18 connecting between the controller 16 and the catheter 12 has a clock/trigger (Clk/Trig) conductor 86 that is detachably connected to a Clk/Trig conductor 88 in the catheter cable 84 that in turn is detachably connected to a Clk/Trig conductor 74 running through the spline system 24. There is also a controller ground (Gnd) conductor 90 connected to a catheter ground conductor 92 in turn connected to a ground conductor 76 in the spline system. A voltage-source (Vsource) conductor 94 in the controller 16 connects to a Vsource conductor 96 in the catheter 12 and onto a Vsource conductor 78 in the spline system 24. Finally, a voltage-output (Vout) conductor 98 connects from a signal conditioning circuit 100 in the controller 16 to a Vout conductor 102 in the catheter 12 and then onto a Vout conductor 80 in the spline system 24. The signal conditioner circuit 100 is electrically connected to the microprocessor 82 of the controller 16.

The Gnd conductor 76, the Vsource conductor 78 and the Vout conductor 80 in the spline system are sequentially connected to a dedicated polling circuit associated with each of the plurality of electrodes. In a sampling sequence, the controller 16 sends a sampling trigger signal (Clk/Trig) to a $1^{st}$ electrode 104 in the first spline 28 of the spline system. In the previously described sampling sequence for the exemplary four-spline system described with respect to FIG. 4, this is the proximal-most electrode in the first spline 28. This initiating signal activates a polling circuit 106 connected to the $1^{st}$ electrode 104. The polling circuit 106 passes the first voltage sample from the electrode 104 to the controller 16 along the Vout conductor 80. In this case, the voltage sample relates to a unipolar Intracardiac Electrogram (EGM), which is the recording of localized electrical activity within the heart, determined as the voltage difference between the intracardiac electrode 104 serving as an anode and a dispersive electrode affixed to the patient's back serving as a cathode. The unipolar EGM can be used to determine the direction of a wave front propagation or a source location.

After the first voltage sample from the $1^{st}$ electrode 104 is sent to the controller 16, the $1^{st}$ electrode polling circuit 106 sends a clock/trigger signal to a $2^{nd}$ electrode 108 to activate the associated polling circuit 110. The $2^{nd}$ electrode 108 is the previously described next most proximal electrode on spline 28. Activation of the $2^{nd}$ polling circuit 110 causes a second unipolar EGM voltage sample to be sent from the $2^{nd}$ electrode 108 to the controller 16 along the Vout conductor 80. This sequencing continues until the previously described proximal-most electrode 112 on the fourth spline 34 is activated by an associated polling circuit 114 (indicated as the $n^{th}$ electrode and $n^{th}$ polling circuit in FIG. 4) to cause an $n^{th}$ unipolar EGM voltage sample to be sent along the Vout conductor 80 to the controller 16 for processing. The controller 16 outputs EGM voltage sample data on a visual display (not shown).

Among other useful information, the controller 16 is programmed to calculate the values of voltage versus time of the cardiac electrical activity at each electrode. This information can be plotted in a 2D or 3D graph or matched to 3D images of the heart to give a time varying 3D plot of electrical activity in the heart. The controller is configured to display or present this information in real-time in any one of a variety of formats that are useful to a physician.

Figure 6A:
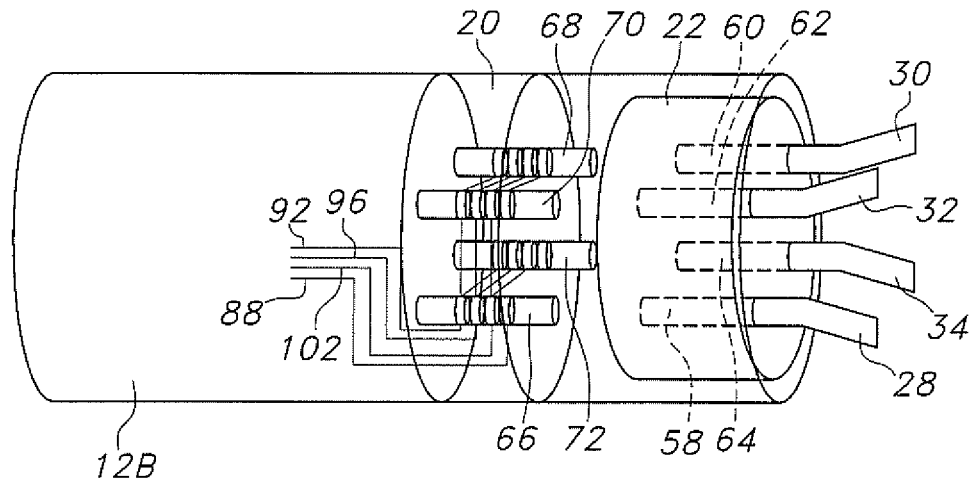
FIG. 6A is an elevational view, partly in phantom, showing the proximal ends of splines 28, 30, 32 and 34 of the spline system 24 shown in FIG. 2 being connected to terminal blocks 72, 66, 68 and 70, respectively, of a distal connector 20 of the catheter 12.
Figure 6B:
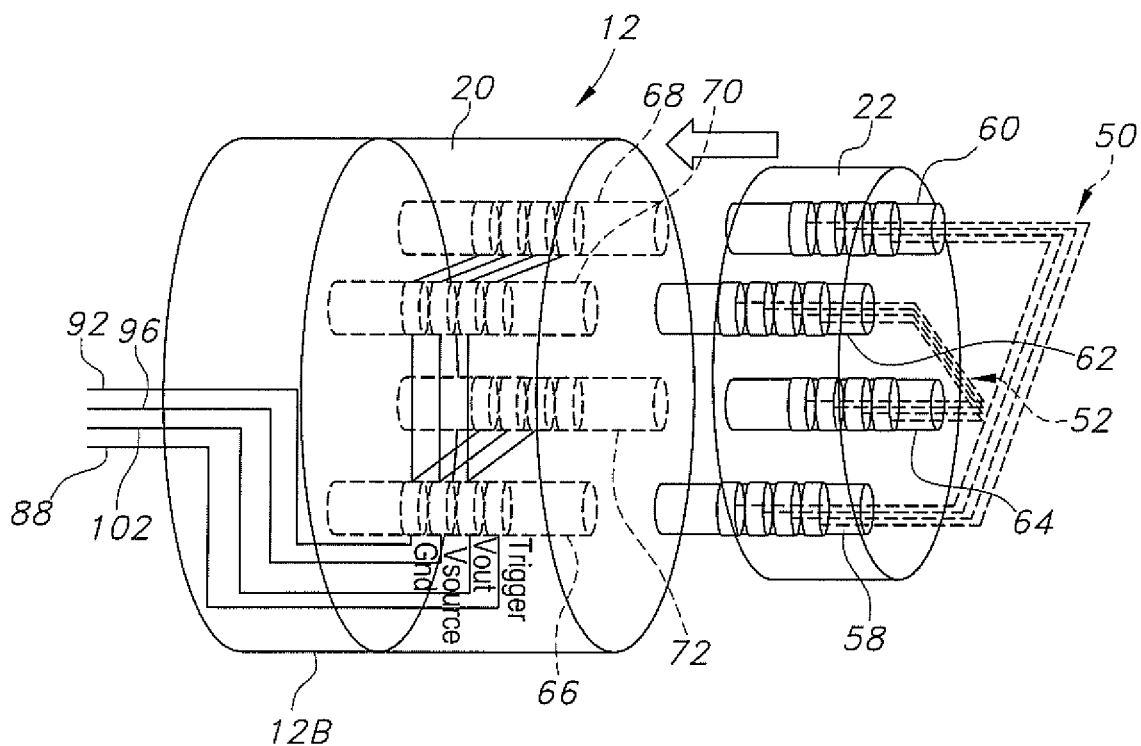
FIG. 6B is an elevational view, partly in phantom, showing the proximal ends of splines 50 and 52 of the two-spline system shown in FIG. 3C being connected to terminal blocks 66/72 and 68/70, respectively, of a distal connector 20 of the catheter 12.

The structure for consecutively sampling the electrical signal from each of a plurality of electrodes in a spline system so that only one Vout conductor is required as illustrated in FIGS. 6A and 6B. As used herein, the term "sample" or "sampling" means a finite EGM voltage measurement of a statistical population of EGM voltage measurements that are used to determine localized electrical activity within the heart.

FIG. 6A is a schematic showing the catheter distal end 12B prior to the proximal anchor 22 of the spline system 24 shown in FIGS. 1 and 2 being connected to the catheter distal connector 20. The proximal anchor 22 is a shaped body of an electrically insulative polymeric material that supports four electrical contacts 58, 60, 62 and 64. The electrical contacts 58, 60, 62 and 64 are electrically connected to respective ones of the splines 28 to 34. The distal connector 20 at the catheter distal end 12B has a corresponding number of terminal blocks 66, 68, 70 and 72 that are sized and shaped to receive the spline electrical contacts 58, 60, 62 and 64 to thereby establish electrical continuity between the catheter 12 and the splines 28, 30, 32 and 34.

Referring now to FIGS. 4, 5 and 6A, an exemplary electrical transmission configuration of the present invention includes electrical conductors 88, 92, 96 and 102 comprising the single catheter cable 84 extending the length of the catheter from the proximal catheter connector 14 to ring-shaped contacts (not numbered) of the first terminal block 66. With the electrical contacts 58, 60, 62 and 64 in the proximal anchor 22 of the spline system 24 being connected to the respective terminal blocks 66, 68, 70 and 72 in the distal connector 20 of the catheter 12, electrical continuity is established from the conductors 88, 92, 96 and 102 of the catheter cable 84 to terminal block 66 connected to electrical connector 58 and then to corresponding Clk/Trig 74, Gnd 76, Vsource 78 and Vout 80 conductors of a single electrical cable (not numbered) extending to the first electrode 104 (FIG. 5) of a first spline 28. Electrical continuity then extends along spline 28 (FIGS. 4 and 5) to the distal anchor 26. Electrical conductors corresponding to the Clk/Trig 74, Gnd 76, Vsource 78 and Vout 80 conductors then connect from the distal anchor 26 to spline 30 and then along that spline to its electrical connector 60 connected to terminal block 68. Electrical conductors corresponding to the Clk/Trig 74, Gnd 76, Vsource 78 and Vout 80 conductors then connect from terminal block 68 to terminal block 70. Terminal block 70 is electrically connected to electrical contact 62 of spline 32. Electrical conductors corresponding to the Clk/Trig 74, Gnd 76, Vsource 78 and Vout 80 conductors extend along spline 32 to the distal anchor 26. Electrical conductors corresponding to the Clk/Trig 74, Gnd 76, Vsource 78 and Vout 80 conductors then connect from the distal anchor 26 to spline 34 and then along that spline to its electrical connector 64 connected to terminal block 72. Electrical conductors corresponding to the Gnd 76, Vsource 78 and Vout 80 conductors, but not the Clk/Trig 74 conductor, then connect from the terminal block 72 back to terminal block 66, which is electrically connected to the catheter cable 84. The catheter cable 84 with electrical conductors 88, 92, 96 and 102 extends proximally through the catheter 12 to connect to the proximal connector 14, which in turn is electrically connected to the controller 16 by the controller cable 18.

FIG. 6B is a schematic showing the catheter distal end 12B prior the spline system shown in FIG. 3C being connected to the catheter distal connector 20. In this case, the electrical contacts 58 and 60 supported by the proximal anchor 22 are electrically connected to the opposite ends of spline 50 and electrical contacts 62 and 64 are electrically connected to the opposite ends of spline 52. As with FIG. 6A, the spline electrical contacts 58, 60, 62 and 64 in the proximal anchor 22 are detachably connectable to the terminal blocks 66, 68, 70 and 72 at the catheter distal connector 20 to thereby establish electrical continuity between the catheter 12 and the splines 50 and 52.

Referring now to FIGS. 4, 5 and 6B, an exemplary electrical transmission configuration of the present invention includes electrical conductors 88, 92, 96 and 102 comprising the single catheter cable 84 extending the length of the catheter from the proximal catheter connector 14 to ring-shaped contacts (not numbered) of the first terminal block 66. With the electrical contacts 58, 60, 62 and 64 in the proximal anchor 22 of the spline system 24 being connected to the respective terminal blocks 66, 68, 70 and 72 in the distal connector 20 of the catheter 12, electrical continuity is established from the conductors 88, 92, 96 and 102 of the catheter cable 84 to terminal block 66 connected to electrical connector 58 and then to corresponding Clk/Trig 74, Gnd 76, Vsource 78 and Vout 80 conductors of a single electrical cable (not numbered) extending to the first electrode 104 (FIG. 5) of a first spline 50. Electrical continuity then extends along spline 50 to spline contact 60 connected to the terminal block 68. Electrical conductors corresponding to the Clk/Trig 74, Gnd 76, Vsource 78 and Vout 80 conductors then connect from terminal block 68 to terminal block 70. The terminal block 70 is electrically connected to electrical contact 62 of spline 52. Electrical conductors corresponding to the Clk/Trig 74, Gnd 76, Vsource 78 and Vout 80 conductors extend along spline 52 to its opposite end connected to spline contact 64 which is electrically connected to catheter terminal block 72. Electrical conductors corresponding to the Gnd 76, Vsource 78 and Vout 80 conductors, but not the Clk/Trig 74 conductor, then connect from terminal block 72 back to terminal block 66, which is electrically connected to the catheter cable 84. The catheter cable 84 with electrical conductors 88, 92, 96 and 102 extends proximally through the catheter 12 to connect to the proximal connector 14, which in turn is electrically connected to the controller 16 by controller cable 18.

Thus, the trigger electrical conductor 88 in the catheter cable 84 connects only to terminal block 66. As will be described in detail later in FIG. 11, in this way, conductor 88 carries the trigger signal to the first electrode sensor station of spline 28/50, thereby initiating an EGM sampling sequence described later.

Figure 7:
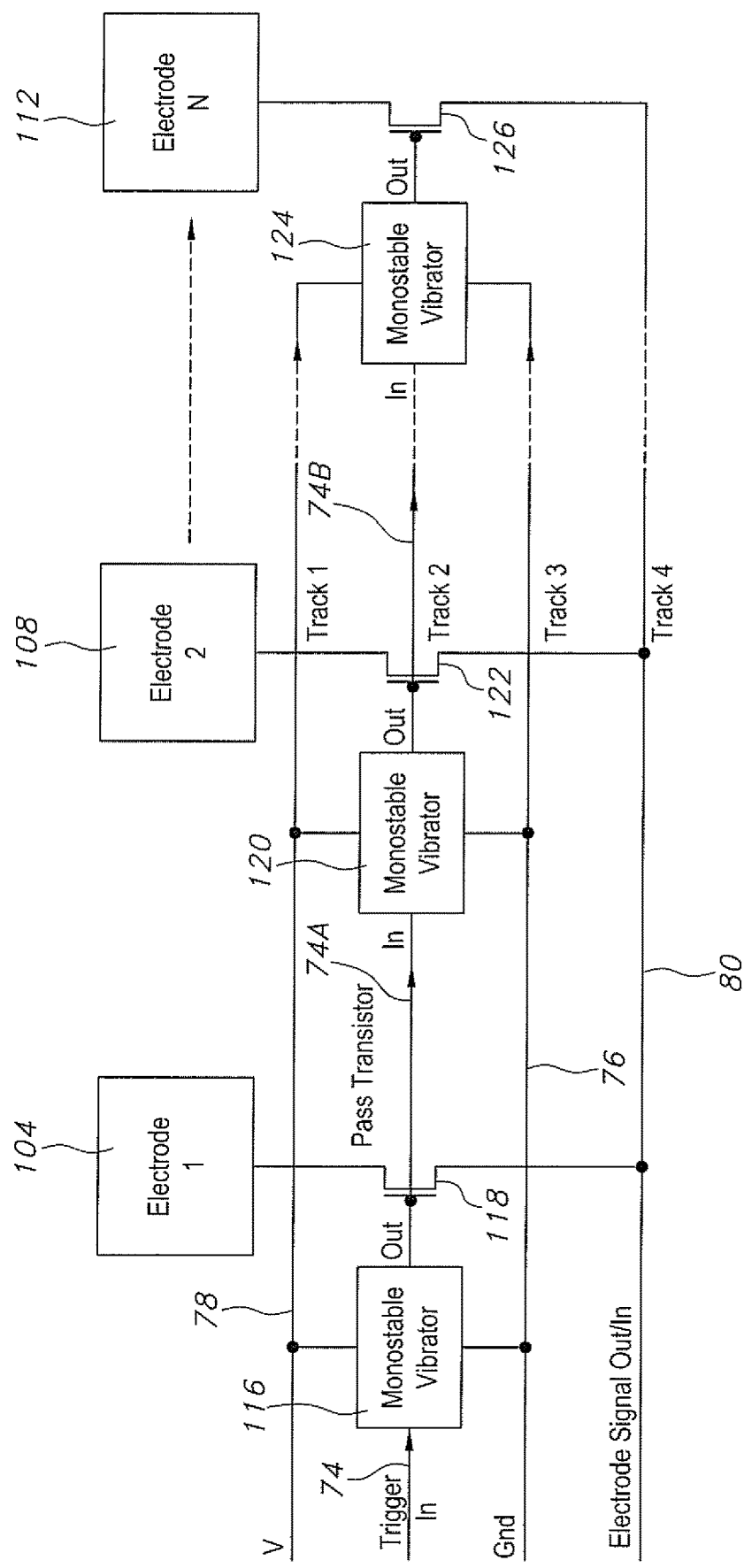
FIG. 7 is a schematic drawing of a consecutive sampling sequence for a unipolar Intracardiac Electrogram (EGM) according to the present invention.

Another embodiment of the present invention related to a unipolar EGM is shown in FIG. 7 where each electrode is electrically connected to an electric circuit consisting of a monostable multivibrator and an N-Channel Enhancement-MOSFET pass transistor or "a one-shot circuit/pass transistor" used as a switching element. When a monostable multivibrator, also called a "one-shot circuit", is triggered, the circuit outputs an electrical pulse of a pre-defined duration. The one-shot circuit then returns to its stable state and does not output an electrical pulse until triggered again. The electrode circuit is powered by a connection to the ground conductor 76 and a connection supply voltage conductor 78.

For the $1^{st}$ electrode 104, the trigger signal on conductor 74 is connected to the trigger input of the monostable multivibrator 116. The output of the monostable multivibrator 116 is connected to the gate of the N-Channel Enhancement-MOSFET 118 and to an inter-sensor trigger signal conductor 74A which in turn is connected to the trigger input of a $2^{nd}$ monostable multivibrator 120 of the next electrode/sensor station circuit.

The electrode 104 is connected to the drain terminal of the N-Channel Enhancement-MOSFET 118 which passes an EGM sample signal to the voltage-out conductor 80 via the source terminal when the MOSFET 118 is ON. Every subsequent electrode to the $n^{th}$ electrode 112 is connected in the same way, but instead of the trigger voltage coming from the controller 16, the trigger voltage enters the $n^{th}$ monostable vibrator 124 connected to the output from the monostable vibrator of the previous electrode along an inter-trigger signal conductor 74B.

Figure 7A:
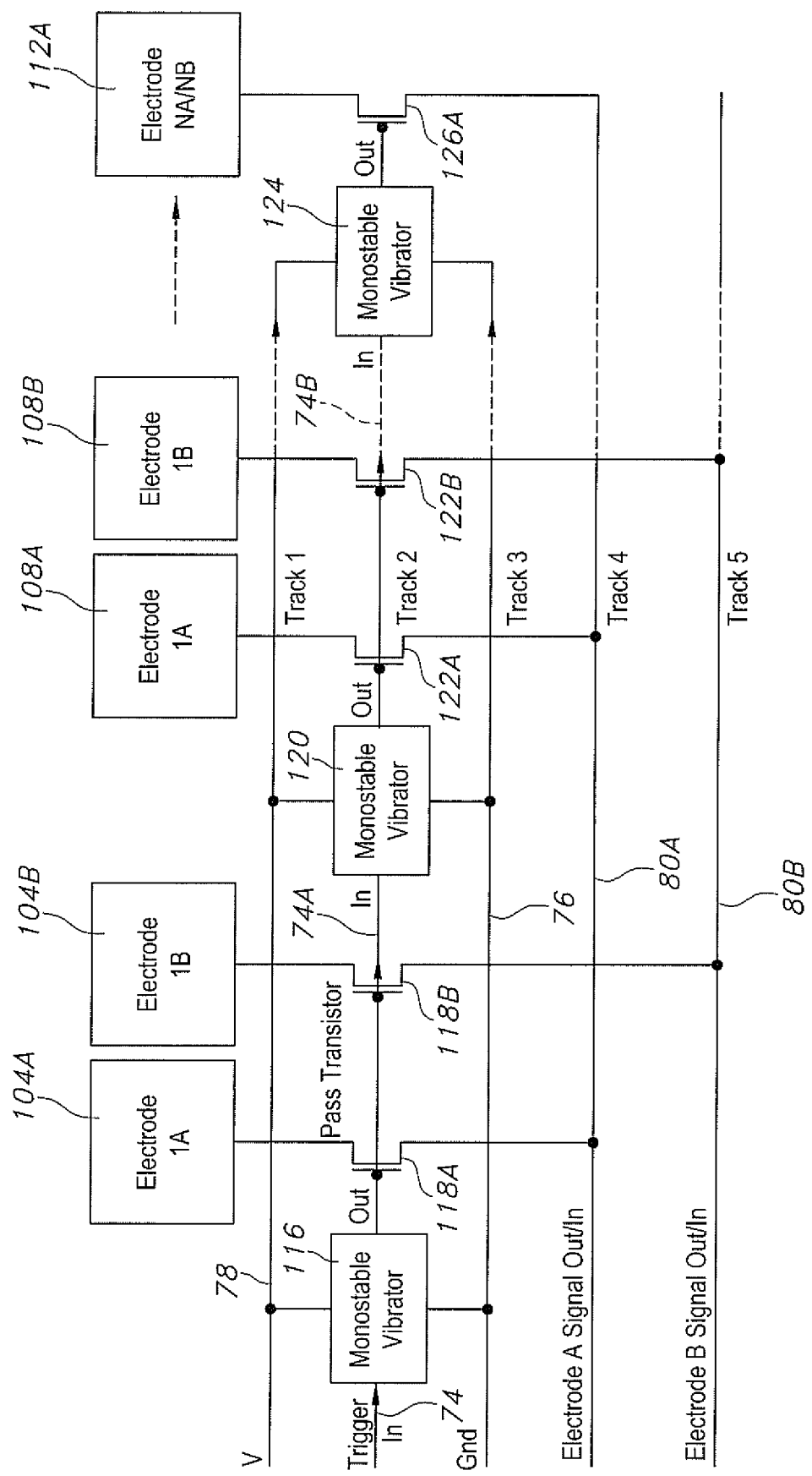
FIG. 7A is a schematic drawing of a consecutive sampling sequence for a bipolar EGM according to the present invention.

FIG. 7A illustrates another embodiment of the present invention for sending bipolar EGM sample signals to the controller 16. A bipolar EGM relates to current flow between adjacent intracardiac catheter electrodes. For adjacent electrodes, typically the distal electrode acts as the cathode, and the proximal electrode is the anode. In this embodiment, the voltages of the two electrodes of a pair are sampled simultaneously and sent to the controller 16 which calculates the voltage difference between the two samples and then sends the difference for display in a suitable form.

Both electrodes of the pair 104A and 104B are electrically connected to an electric circuit consisting of a monostable multivibrator 116 and two N-Channel Enhancement-MOSFET pass transistors 118A and 118B, one MOSFET for each electrode. The gates of the MOSFETs are connected and are also connected to the output of the first monostable multivibrator 116 so that both MOSFETs switch ON or OFF simultaneously when the output from the monostable multivibrator 116 is high or low, respectively. The output of the monostable multivibrator is also connected directly to the trigger input of the monostable multivibrator of the next circuit via the inter-sensor trigger signal conductor 74A.

When the monostable multivibrator 116 is triggered, the one-shot circuit outputs an electrical pulse of a pre-defined duration to the gates of the N-Channel Enhancement-MOSFETs 118A and 118B associated with the pair of electrodes 104A and 104B and to the monostable vibrator 120 of the next circuit before returning to its stable state.

When the output from the monostable multivibrator is high, the gates of both MOSFETs go high thereby switching the MOSFETs ON so that the voltage on electrode 104A is passed via the drain and source of the first MOSFET 118A to conductor 80A and simultaneously the voltage on electrode 104B is passed via the drain and source of the second MOSFET 118B to conductor 80B. The monostable multivibrator 120 of the next circuit is not triggered until the falling edge of the electrical pulse output from the monostable multivibrator 116 arrives at the trigger input of the monostable multivibrator 120 at the end of the pulse. As will be seen below, this ensures that voltages from electrodes 108A and 108B are not being passed onto conductors 80A and BOB, respectively, at the same time as voltages from electrodes 104A and 104B are being passed onto the conductors 80A and BOB, respectively.

Continuing, for the $2^{nd}$ pair of electrodes 108A and 108B, which are also electrically connected to an electric circuit consisting of a monostable multivibrator 120 and two N-Channel Enhancement-MOSFET pass transistors 122A and 122B, one MOSFET is provided for each electrode. The gates of the MOSFETs 122A and 122B are connected and are also connected to the output of the second monostable multivibrator 120 so that both MOSFETs 122A, 122B switch ON or OFF simultaneously when the output from the monostable multivibrator 120 is high or low, respectively. The output of the monostable multivibrator is also connected directly to the trigger input of the monostable multivibrator of the next circuit via the inter-sensor trigger signal conductor 74B.

When the monostable multivibrator 120 is triggered by the falling edge of the output electrical pulse of monostable multivibrator 116, it outputs an electrical pulse of a pre-defined duration to the gates of the N-Channel Enhancement-MOSFETs 122A and 122B associated with the pair of electrodes 108A and 108B and to the monostable multivibrator of the next circuit before returning to its stable state. When the output from the monostable multivibrator is high, then the gates of both MOSFETs 122A and 122B go high thereby switching the MOSFETs ON so that the voltage on electrode 108A is passed, via the drain and source of the MOSFET 122A, to conductor 80A and simultaneously the voltage on electrode 108B is passed, via the drain and source of the MOSFET 122B, to conductor 80B. The monostable multivibrator of the next circuit is not triggered until the falling edge of the electrical pulse output from the monostable multivibrator 120 arrives at the trigger input of the next monostable multivibrator at the end of the output pulse from monostable multivibrator 120.

The output of the monostable multivibrator 120 is connected to the next circuit via the inter-sensor trigger signal conductor 74B which is connected to the trigger input of the monostable multivibrator 124 connected to the next or $n^{th}$ electrode 112A. This sequencing continues until each electrode of all the pairs of electrodes has been sampled. Upon completion of a full sampling sequence, the controller 16 initiates another sampling sequence beginning with the first pair of electrodes 104A/104B.

Figure 8:
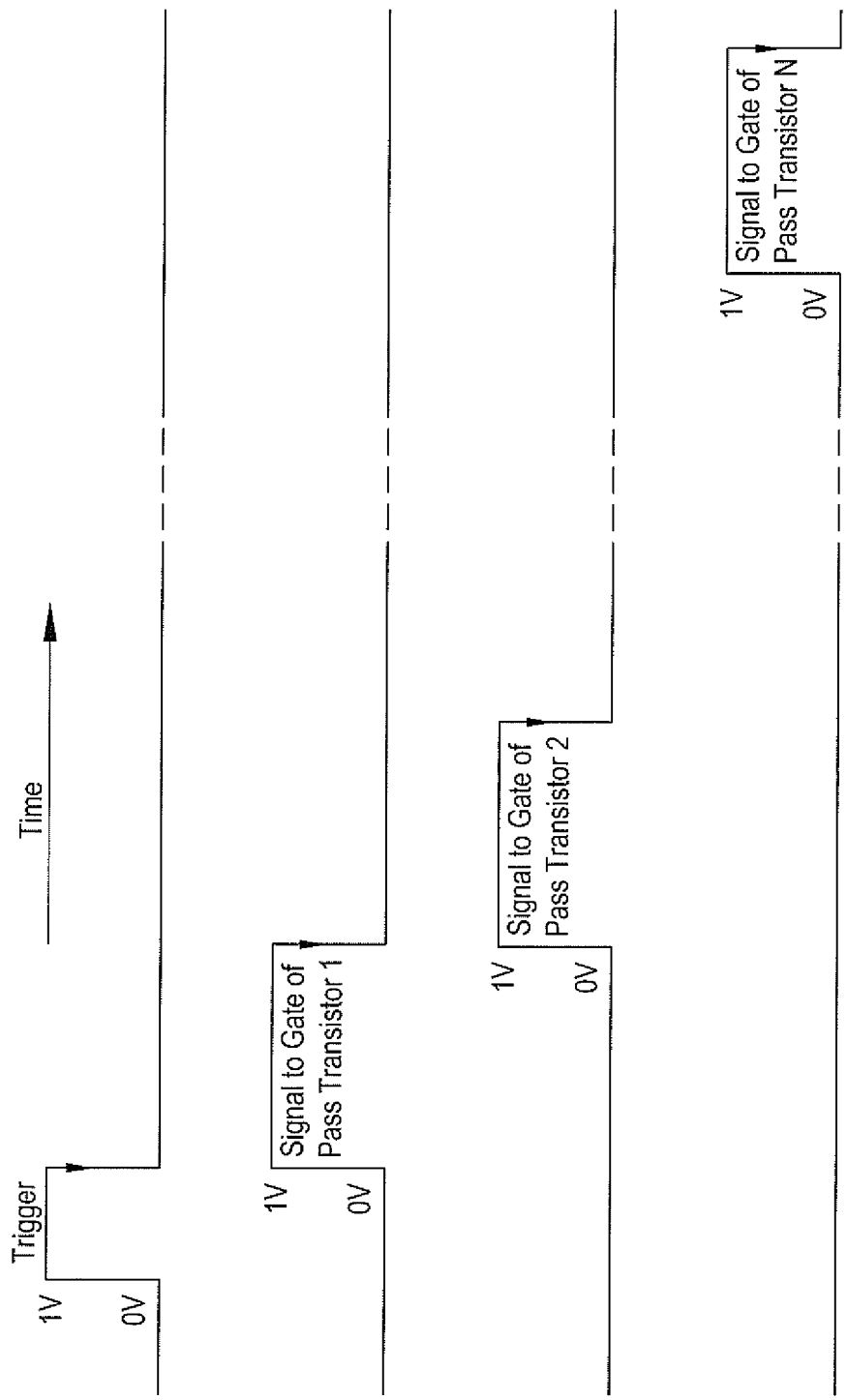
FIG. 8 is a graph depicting the trigger signal for sequentially activating the sampling electrodes of the basket-type EP catheter system 10 of the present invention.

As shown in FIG. 8, during a sampling sequence, the monostable multivibrator of an electrode circuit is triggered by the falling edge of a positive pulse on the trigger input. A single positive pulse of pre-defined duration is produced on the monostable multivibrator output which is applied to the gate of the N-Channel Enhancement-MOSFET so that the MOSFET is switched to the ON state to act as a closed switch. In this case, the electrode voltage which is applied through the N-Channel Enhancement-MOSFET drain terminal is fed to the Vout conductor 80 connected to the source terminal. When the gate voltage is zero, the MOSFET is in the OFF state and acts as an open switch so that an EGM voltage sample is not fed to the Vout conductor 80. During the falling edge of the output of the monostable multivibrator, the N-Channel Enhancement-MOSFET of the electrode switches to the OFF state and the monostable multivibrator of a next or second electrode is triggered by this falling edge. In this way, the voltage at each electrode is consecutively passed to the Vout conductor 80 for a fixed duration so that it is not possible for two EGM voltage samples to be passed to the electrical signal track/conductor 80 simultaneously.

Figure 9:
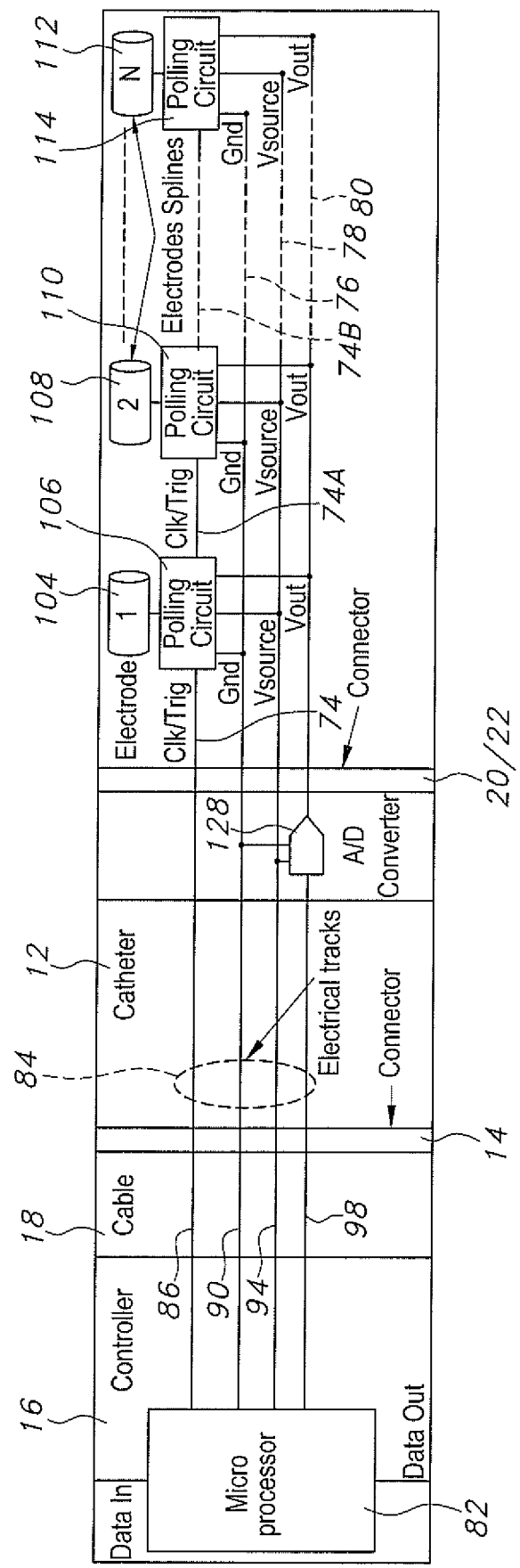
FIG. 9 is a schematic drawing of a simplified form of a consecutive sampling sequence produced by the basket-type EP catheter system 10 with an analog-to-digital (A/D) converter located at the distal end of the catheter 12.

FIG. 9 is a schematic drawing showing a sampling sequence according to the present invention that is similar to the electrode sampling sequence schematically illustrated in FIG. 5, but with the addition of an analog-to-digital (A/D) converter 128 electrically connected between the catheter 12 and the distal connector 20. The reason is to avoid sending an EGM voltage sample as an analog signal down the length of the catheter cable 84 of the catheter 12 where the voltage signal could degrade due to variations in impedance and due to EM noise. Digital signals do not degrade in a similar manner as analogue signals do.

Figure 10:
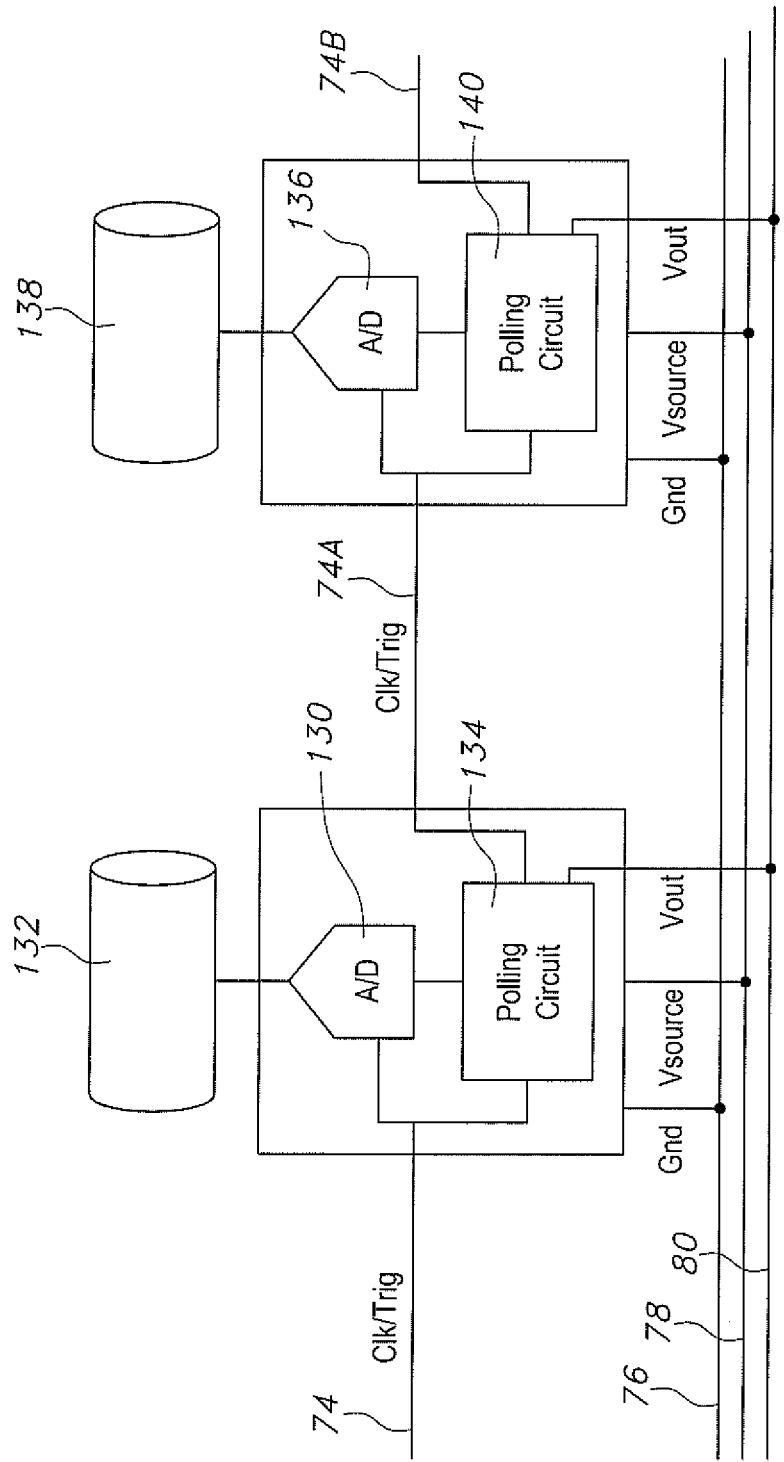
FIG. 10 is a schematic drawing of a simplified form of a consecutive sampling sequence produced by the basket-type EP catheter system 10 with an A/D converter 130 electrically connected between the $1^{st}$ electrode 132 and its polling circuit 134 and between the $2^{nd}$ electrode 138 and its polling circuit 140.

Ideally the A/D converter 128 is positioned as close as possible to the electrodes in the spline system 24. The optimum construction is to position the A/D converter in the electrode circuit. This is shown in FIG. 10 where an A/D converter 130 is electrically connected between the $1^{st}$ electrode 132 and its polling circuit 134. Similarly, an A/D converter 136 is electrically connected between the $2^{nd}$ electrode 138 and its polling circuit 140. This construction continues for each of the electrodes in the spline system 24 to the $n^{th}$ electrode.

The next optimum construction is to position the A/D converter at the distal end 12B of the catheter 12 as previously shown in FIG. 9. The A/D converter can also be in the controller 16.

Figure 11:
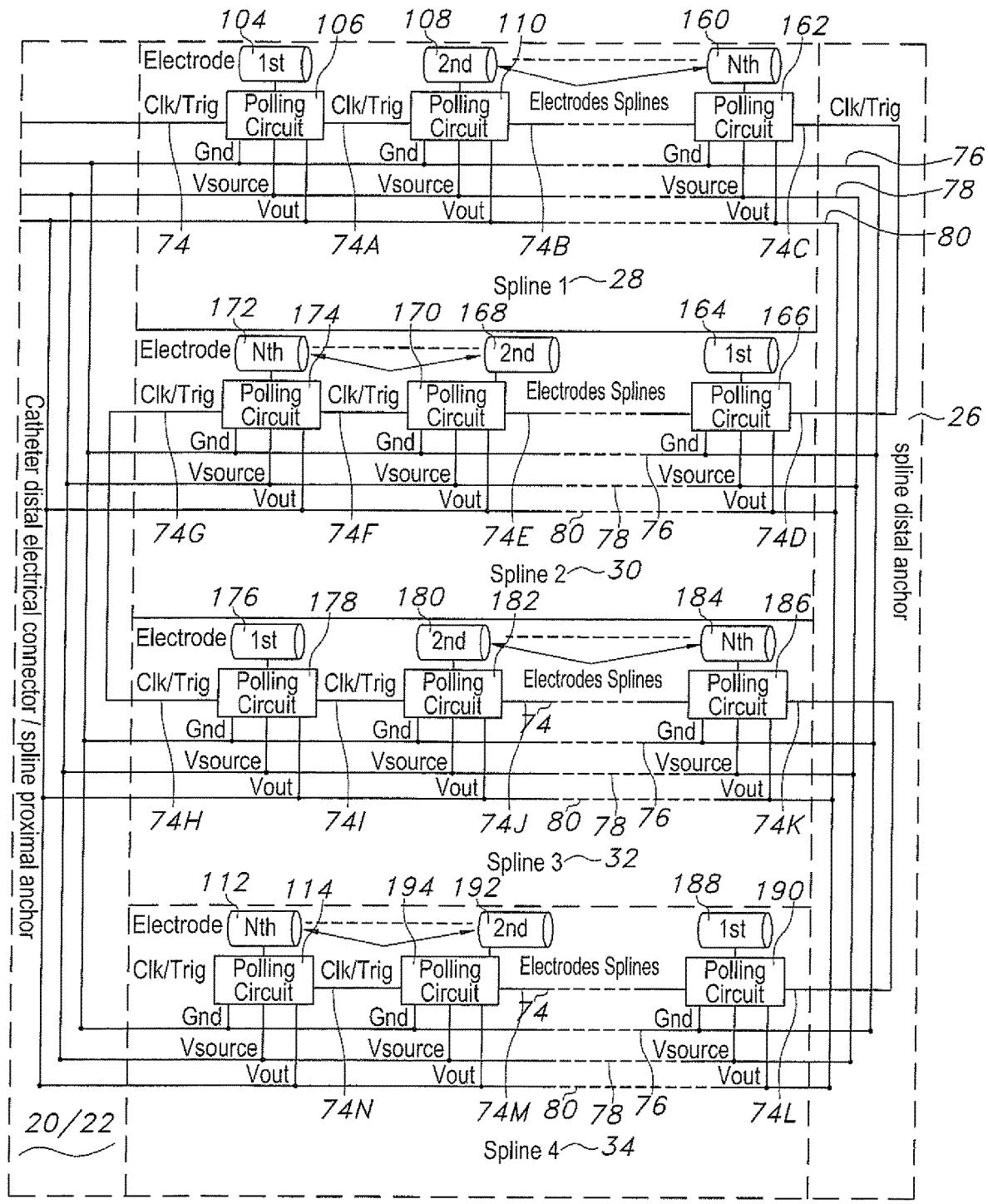
FIG. 11 is a schematic drawing showing the consecutive sampling sequence produced by the basket-type EP catheter system 10 having a four-spline system.

Having a fundamental understanding of a sampling sequence according to the present invention, one can see that FIG. 11 depicts a four-spline system similar to that shown in FIGS. 2 and 5. In a sampling sequence, the controller 16 sends a sampling trigger signal (Clk/Trig) along the catheter cable 84 and onto the conductor 74 in the first spline 28 to the $1^{st}$ electrode 104. The trigger signal activates the polling circuit 106 connected to the $1^{st}$ electrode 104. The polling circuit 106 passes the first Intracardiac Electrogram (EGM) voltage sample from the electrode 104 to the controller 16 along the Vout conductor 80. The $1^{st}$ electrode polling circuit 106 then sends a clock/trigger signal along inter-trigger signal conductor 74A to the $2^{nd}$ polling circuit 110 to activate the $2^{nd}$ electrode 108. Activation of the $2^{nd}$ polling circuit 110 causes a second EGM voltage sample to be sent from the $2^{nd}$ electrode 108 to the controller 16 along conductor 80. This sequencing continues along the first spline 28 until the distal-most or $n^{th}$ electrode 160 on that spline is activated by its associated polling circuit 162. The polling circuit 162 sends an EGM voltage sample from the electrode 160 to the controller 16 along the Vout conductor 80.

Sequencing on the second spline 30 begins with the $n^{th}$ polling circuit 162 on the first spline 28 sending a clock/trigger signal inter-trigger signal along conductor 74C to the distal connector 26 and then to conductor 74D connected to the let polling circuit 166 to activate the $1^{st}$ electrode 164 on the second spline 30. After sending an EGM sample to the controller 16, the $1^{st}$ polling circuit 166 sends a clock/trigger signal along inter-trigger signal conductor 74E to the $2^{nd}$ polling circuit 170 to activate the $2^{nd}$ electrode 168 on the second spline 30. This causes an EGM sample to be sent from the $2^{nd}$ polling circuit 170 to the controller 16 for processing. This sequencing continues along spline 30 until the proximal-most or $n^{th}$ electrode 172 on that spline 30 is activated by its associated polling circuit 174 triggered by a trigger signal along inter-trigger signal conductor 74F from the previous most adjacent polling circuit and an EGM voltage sample is sent to the controller 16.

Sequencing on the third spline 32 begins with the $n^{th}$ polling circuit 174 on the second spline 30 sending a clock/trigger signal along inter-trigger signal conductor 74G to the proximal connector 22 and then to conductor 74H connected to the $1^{st}$ polling circuit 178 to activate the $1^{st}$ electrode 176 on the third spline 32. After sending an EGM sample to the controller 16, the $1^{st}$ polling circuit 178 sends a clock/trigger signal along inter-trigger signal conductor 74I to the $2^{nd}$ polling circuit 182 to activate the $2^{nd}$ electrode 180 on the third spline 32. This causes an EGM sample to be sent from the $2^{nd}$ polling station 182 on the third spline 32 to the controller 16 for processing. This sequencing continues along spline 32 until the proximal-most or $n^{th}$ electrode 184 on that spline 32 is activated by its associated polling circuit 186 triggered by a trigger signal along inter-trigger signal conductor 74J from the previous most adjacent polling circuit and an EGM voltage sample is sent to the controller 16.

Sequencing on the fourth spline 34 begins with the $n^{th}$ polling circuit 186 on the third spline 32 sending a clock/trigger signal along inter-trigger signal conductor 74K to the distal connector 26 and then to conductor 74L connected to the $1^{st}$ polling circuit 190 to activate the electrode 188 on the fourth spline 34. The $1^{st}$ polling circuit 190 then sends a clock/trigger signal to the $2^{nd}$ polling circuit 194 along inter-trigger signal conductor 74M to activate the $2^{nd}$ electrode 192 on the fourth spline 34. This causes an EGM sample to be sent from the $2^{nd}$ electrode 192 to the controller 16 for processing. This sequencing continues along spline 34 until the previously described proximal-most electrode 112 on the fourth spline 34 is activated by its associated polling circuit 114 triggered by a trigger signal along inter-trigger signal conductor 74N from the previous most adjacent polling circuit and an EGM voltage sample is sent to the controller 16.

This completes one full sampling sequence for the four-spline system illustrated in FIGS. 2 and 5. Upon completion of the sampling sequence, the controller 16 initiates a subsequent sampling sequence by sending a clock/trigger signal along the catheter cable 84 and onto the conductor 74 to the $1^{st}$ polling circuit 106 corresponding to the $1^{st}$ electrode 104 on the first spline 28, as previously described.

Referring now to FIGS. 12A to 12D, an exemplary embodiment of a spline for the spline systems according to the present invention is illustrated. The spline is in the form of an elongate flex circuit 200 supporting electrical conductors or tracks extending from a proximal end 200A to various contact pads grouped on a land 202. The electrical conductors or tracks can be either supported on the flex circuit 200 or embedded therein. The clock/trigger conductor 74 extends along the flex circuit to a clock/trigger in (Trig-in) contact pad 204A supported on the land 202, the ground conductor 76 extends to a ground contact pad 206 (indicated with the minus "−" symbol), the Vsource conductor 78 extends to a positive polarity contact pad 208 (indicated with the plus "+" symbol), and the Vout conductor 80 extends to a voltage-out contact pad 210 on land 202. A contact pad 212 labeled "in" on the land 202 of the flex circuit 200 extends from conductor 214. There is also a clock/trigger out (Trig-out) contact pad 204B from which conductor 74A extends.

Figure 12A:
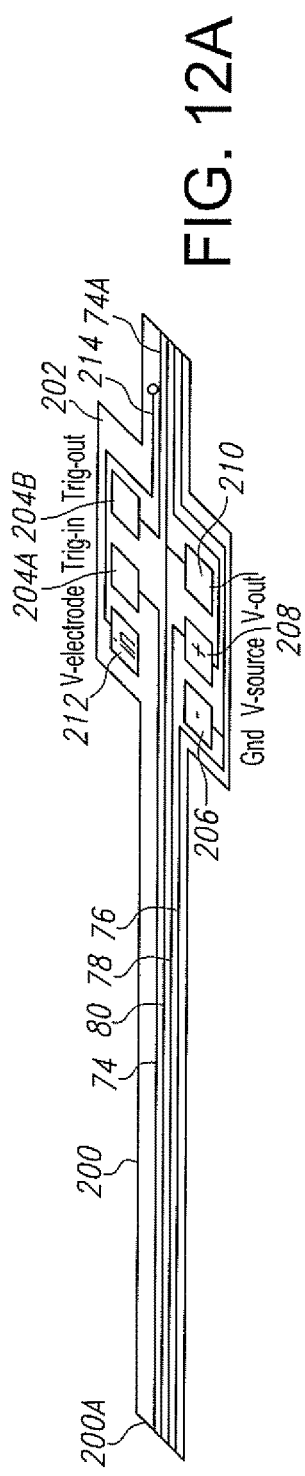
FIGS. 12A to 12D are schematic drawings showing an embodiment of a spline formed from a flexible circuit 200 for the basket-type EP catheter system 10 of the present invention.
Figure 12B:
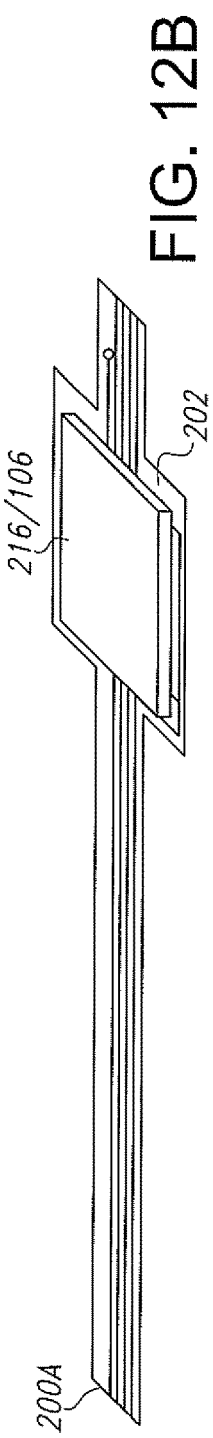

FIG. 12B shows that an IC or integrated circuit 216 is supported on the land 202 of the flex circuit 200. While not shown in the drawing, the IC circuit 216 has electrical contacts that align with and make electrical connection to the contact pads 204A, 204B, 206, 208, 210 and 212. With reference to the exemplary spline system shown in FIG. 5, the polling circuit 106 is incorporated into the IC circuit 216.

Figure 12C:
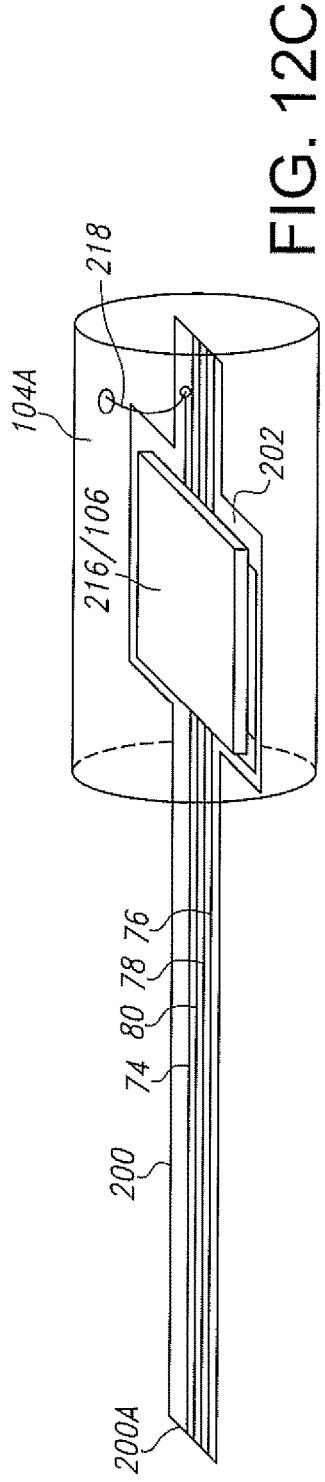
Figure 12D:
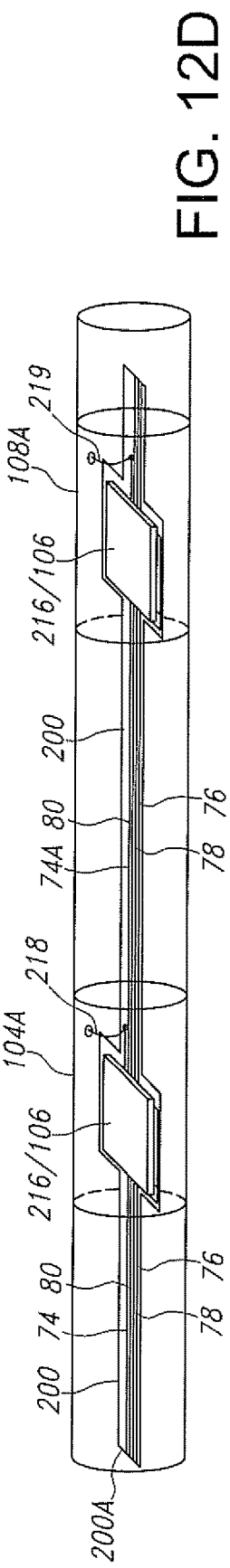

FIG. 12C shows that the first electrode 104 in FIG. 5 is a ring-shaped electrode 104A having a cylindrical shape. The IC circuit 216 supported on the land 202 of the flex circuit 200 is housed inside the ring-shaped electrode 104A. A connecter wire 218 connects from the IC/polling circuit 216/106 to the ring-shaped electrode 104A. This is how the electrical connection is made from the polling circuit 106 in FIG. 5 to the first electrode 104. The second ring-shaped electrode 108A shown in FIG. 12D coincides with the second electrode 108 associated with the polling circuit 110 depicted in FIG. 5. A connecter wire 219 connects from the IC/polling circuit 216/110 to the ring-shaped electrode 108A.

As previously described, in a sampling sequence the controller 16 sends a sampling trigger signal (Clk/Trig) along the catheter cable 84 and along conductor 74 to initiate signal activation of the polling circuit 106 for the $1^{st}$ electrode 104A. The polling circuit 106 then passes the first EGM voltage sample from the electrode 104A to the controller 16 along the Vout conductor 80. The $1^{st}$ polling circuit 106 then sends a clock/trigger signal to the $2^{nd}$ electrode 108A along conductor 74A to activate its polling circuit 110. A second unipolar EGM voltage sample is then sent from the $2^{nd}$ electrode 108A to the controller 16 along Vout conductor 80. This sequencing continues until the previously described $n^t$ electrode and $n^{th}$ polling circuit in FIG. 5 are activated to cause an $n^{th}$ unipolar EGM voltage sample to be sent along the Vout conductor 80 to the controller 16 for processing and appropriate display.

Figure 13B:
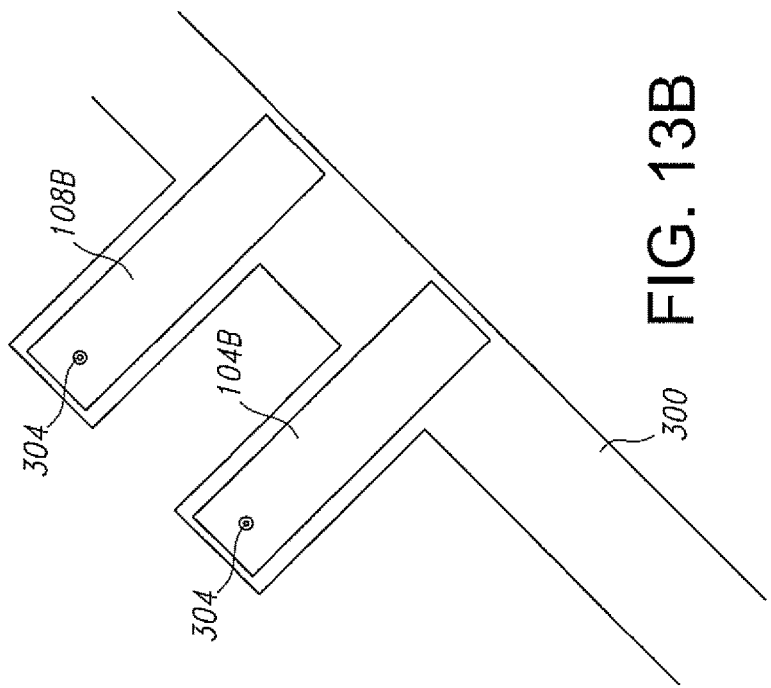
FIGS. 13A to 13C are schematic drawings showing an embodiment of a spline formed from a flexible circuit 300 with electrodes 104B and 108B supported on a cylindrically-shaped insulator 306 for the basket-type EP catheter system 10 of the present invention.
Figure 13A:
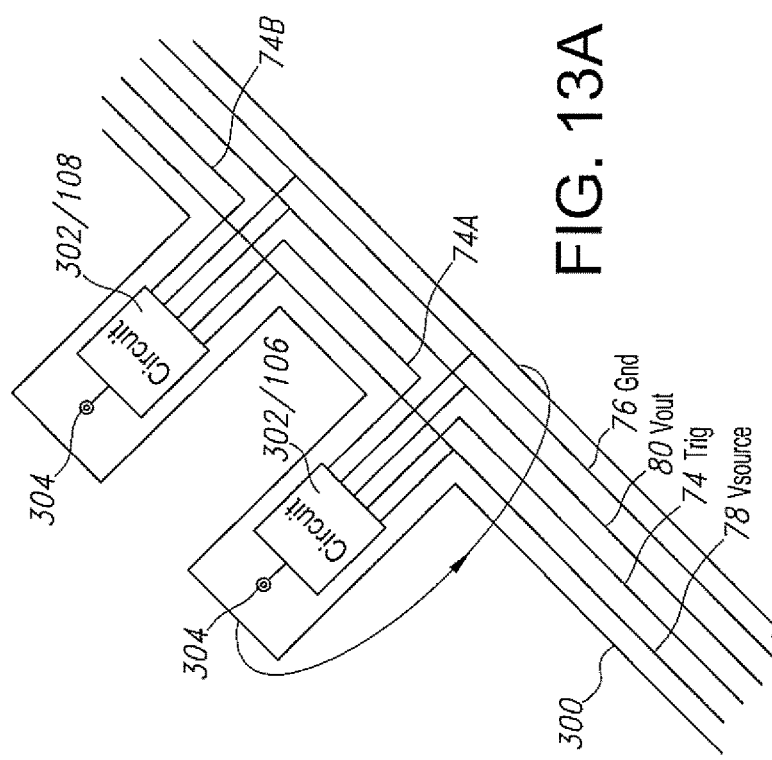
Figure 13C:
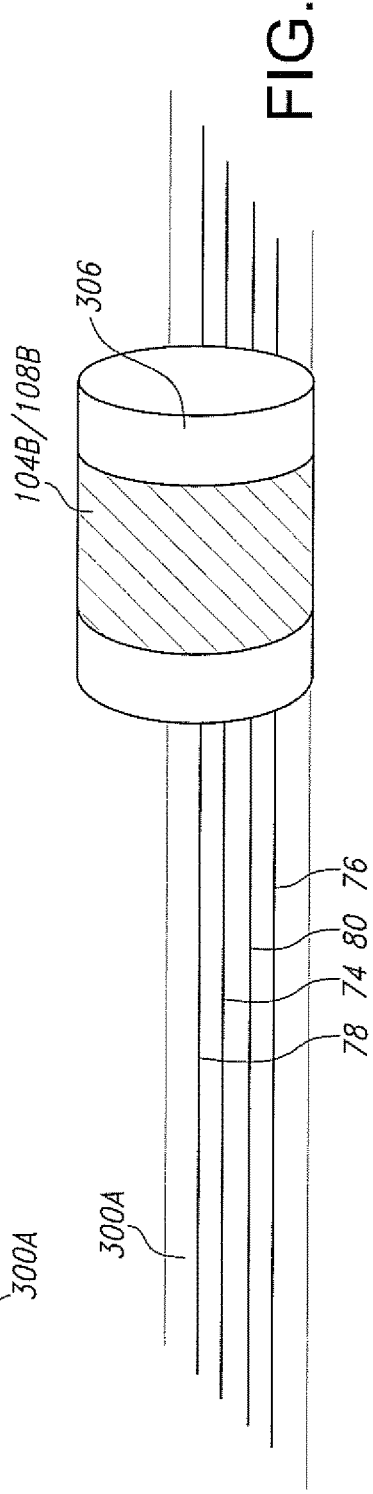

FIGS. 13A to 13C illustrate another exemplary embodiment of a spline for a spline system according to the present invention. The spline comprises an elongate flex circuit 300 supporting electrical conductors or tracks extending from a proximal end 300A of the spline to various contact pads grouped on a land. The electrical conductors or tracks can be either supported on the flex circuit 200 or embedded therein. An IC or integrated circuit 302 is supported on the land of the flex circuit 300. The IC circuit 302 has electrical contacts that align with and make electrical connection to contact pads similar to those described with respect to FIGS. 12A to 12D for the clock/trigger contact pads 204A and 204B, the ground contact pad 206, the voltage supply contact pad 208, and the voltage-out contact pad 210. With reference to the exemplary spline system, the polling circuit 106 shown in FIG. 5 is incorporated into the IC circuit 302.

A via hole 304 extending through the thickness of the flexible substrate for the flex circuit 300 provides a conductive pathway to a flexible plate-shaped electrode 104B supported on the opposite side of land for the flex circuit. The flexible electrode 104B is then wrapped around the cylindrically-shaped insulator 306 shown in FIG. 13C. This flexible electrode supported on a cylindrically-shaped insulator structure is repeated to provide a spline with as many sampling electrodes as are desired for an application. Otherwise, the fundamental aspects of a spline-based sampling system for providing EGM samples to a controller for analysis and output apply is as has been previously described.

While not shown in the drawings, the proximal end 12A of the catheter 12 for the basket-type EP catheter system 10 of the present invention is configured to connect to a handle assembly. In one embodiment, the handle assembly houses a steering and locking mechanism that provides for selective deflection or steering of the catheter 12 and the detachable spline system 24 into any number of disparate orientations within the vasculature of a patient and then for locking the catheter in a desired orientation for performing a medical procedure. For a more thorough understanding of catheter handles that are useful with the present basket-type EP catheter system 10, reference is made to U.S. Design Pat. No. D612,044 to Scheibe, U.S. Pat. No. D638,934 to Kimmel, U.S. Pat. No. D653,335 to Kampa et al. and U.S. Pat. No. D653,337 to Kampa et al., all of which are assigned to the assignee of the present invention and incorporated herein by reference.

For a more thorough understanding of deflectable catheter steering and locking systems that are useful with the present basket-type EP catheter system 10, reference is made to U.S. Pat. No. 7,497,853 to Fischer et al., U.S. Pat. No. 7,588,555 to Pudelko et al., U.S. Pat. No. 7,615,044 to Scheibe et al., U.S. Pat. No. 7,955,314 to Fischer et al., U.S. Pat. No. 8,007,463 to Pudelko et al., U.S. Pat. No. 8,048,026 to Fischer et al., U.S. Pat. No. 8,308,659 to Scheibe et al., U.S. Pat. No. 8,444,626 to Fischer et al., U.S. Pat. No. 8,790,362 to Kimmel et al. and U.S. Pat. No. 9,149,607 to Scheibe et al., all of which are assigned to the assignee of the present invention and incorporated herein by reference.

For a more thorough understanding of push-pull wire systems including their anchoring mechanisms that are useful with the present basket-type EP catheter system 10, reference is made to U.S. Pat. Nos. 7,553,305, 8,056,207 and 8,540,697, all to Honebrink et al. and all of which are assigned to the assignee of the present invention and incorporated herein by reference. And, for a more thorough understanding of an anchor for a push-pull wire system, reference is made to U.S. Pat. No. 7,497,853 to Fischer et al., which is assigned to the assignee of the present invention and incorporated herein by reference.

In Use

In what is referred to as a transseptal approach in an exemplary cardiac ablation therapy to correct for atrial arrhythmia, an introducer sheath is introduced through a peripheral vein (typically a femoral vein) and advanced into the right atrium of a patient's cardiac muscle. After the introducer sheath is used to make an incision in the fossa ovalis (the tissue wall between the left and right atriums), the introducer is moved through the incision and anchored in the fossa ovalis. Next, the basket-type EP catheter system 10 of the present invention is steered or guided through the left atrium to orient the spline system 24 in a desired location within the left atrium, such as in proximity to a pulmonary vein where an ablation therapy is to be applied.

In an embodiment without push-pull wires, the physician advances the catheter body 12 and its spline system 24 toward a target myocardial site under fluoroscopy-guided observation. In an alternate embodiment with push-pull wires, the physician manipulates the handle assembly connected to the proximal end 12A of the catheter to selectively tension and relax the push-pull wires to control the orientation of the distal spline system 24 as it is advanced under fluoroscopy-guided observation toward a target myocardial site.

After determining that the distal electrode-carrying spline section of the catheter is in stable and steady contact with the endocardium surface of the heart chamber of interest, the EP catheter 10 of the present invention is used to generate an electro-anatomical map (EAM) of heart tissue. The goal is to determine the anatomical structure and physiological health of the heart. This is done by initiating many consecutive electrode sampling sequences where EGM samples indicative of electrical activity of the heart are sent from the various electrodes of the spline system 24 to the controller 16 for analysis and output to the physician in a useful format. Electrical activity is usually measured sequentially on a point-by-point basis at about 50 to 200 locations on the endocardium surface of the heart to construct an electro-anatomical depiction of the heart. The generated map then serves as the basis for deciding on a therapeutic course of action, for example, tissue ablation, to alter the propagation of the heart's electrical activity and to restore normal heart rhythm.

An accurate representation of cardiac anatomy is also useful for other medical applications such as congestive heart failure, injection of biologics into the heart and into scar tissue, anatomical guidance of biopsies, minimally invasive valve repair and replacement, and the like.

It is appreciated that various modifications to the inventive concepts described herein may be apparent to those of ordinary skill in the art without departing from the spirit and scope of the present invention as defined by the appended claims.

What is claimed is:

1. A catheter system, comprising:
   a) a controller;
   b) a flexible, elongate catheter extending from a catheter proximal connector to a catheter distal connector, the catheter proximal connector being electrically connectable to the controller;
   c) at least a first spline extending from a spline proximal anchor to a spline distal anchor, the spline proximal anchor being electrically connectable to the catheter distal connector, wherein the first spline comprises a first spline ground (Gnd) conductor, a first spline voltage-source (Vsource) conductor, and a first spline voltage-out (Vout) conductor, and wherein at least three electrodes are supported by the first spline, the at least three electrodes comprising a first spline first electrode located closest to the spline proximal anchor, a first spline second electrode, and a first spline third electrode located furthest from the spline proximal anchor,
d) wherein, with the catheter proximal connector electrically connected to the controller and with the spline proximal anchor electrically connected to the catheter distal connector, the controller is configured to initiate a first electrode sampling sequence along the first spline comprising a first Clk/Trig conductor connected to a first spline first monostable vibrator connected to a first spline first N-channel Enhancement MOSFET pass transistor, by:
   i) sending a first clock/trigger (Clk/Trig) signal along the first Clk/Trig conductor to trigger the first spline first monostable vibrator to send a second Clk/Trig signal along a second Clk/Trig conductor and to activate the first spline first N-channel Enhancement MOSFET pass transistor connected to the first spline first electrode to transmit a first spline first electrode voltage sample along the first spline Vout conductor to the controller, and
   ii) wherein the second Clk/Trig conductor is connected to a first spline second monostable vibrator connected to a first spline second N-channel Enhancement MOSFET pass transistor, and wherein the second Clk/Trig signal triggers the first spline second monostable vibrator to send a third Clk/Trig signal along a third Clk/Trig conductor and to activate the first spline second N-channel Enhancement MOSFET pass transistor connected to the first spline second electrode to transmit a first spline second electrode voltage sample along the first spline Vout conductor to the controller, and
   iii) wherein the third Clk/Trig conductor is connected to a first spline third monostable vibrator connected to a first spline third N-channel Enhancement MOSFET pass transistor, and wherein the third Clk/Trig signal triggers the first spline third monostable vibrator to activate the first spline third N-channel Enhancement MOSFET pass transistor connected to the first spline third electrode to transmit a first spline third electrode voltage sample along the first spline Vout conductor to the controller, and
   iv) wherein the first spline Gnd and Vsource conductors extend from the spline proximal anchor to at least the first spline first, second and third monostable vibrators.

2. The catheter system of claim 1, wherein, with the at least first spline contacting cardiac tissue, the first spline first, second and third electrode voltage samples relate to respective unipolar Intracardiac Electrogram (EGM) voltage samples.

3. The catheter system of claim 1, wherein transmitting the first spline third electrode voltage sample to the controller triggers the controller to initiate a second electrode sampling sequence by sending a first Clk/Trig signal along the first Clk/Trig conductor to trigger the first spline first monostable vibrator to send a second Clk/Trig signal along the second Clk/Trig conductor and to activate the first spline first N-channel Enhancement MOSFET pass transmitter connected to the first spline first electrode to transmit a first spline first electrode voltage sample along the first spline Vout conductor to the controller.

4. The catheter system of claim 1, wherein there are at least two splines comprising the first spline and a second spline, the second spline extending from the spline proximal anchor to the spline distal anchor, and wherein the second spline comprises a second spline ground (Gnd) conductor, a second spline voltage-source (Vsource) conductor, and a second spline voltage-out (Vout) conductor, and wherein at least three electrodes are supported by the second spline, the at least three electrodes comprising a second spline first electrode located closest to the spline proximal anchor, a second spline second electrode, and a second spline third electrode located furthest from the spline proximal anchor,
   i) wherein the third Clk/Trig signal from the first spline first monostable vibrator also triggers the first spline third monostable vibrator to send a fourth Clk/Trig signal along a fourth Clk/Trig conductor connected to a second spline third monostable vibrator connected to a second spline third N-channel Enhancement MOSFET pass transistor, and wherein the fourth Clk/Trig signal triggers the second spline third monostable vibrator to send a fifth Clk/Trig signal along a fifth Clk/Trig conductor and to activate the second spline third N-channel Enhancement MOSFET pass transistor connected to the second spline third electrode to transmit a second spline third electrode voltage sample along the second spline Vout conductor to the controller, and
   ii) wherein the fifth Clk/Trig conductor is connected to a second spline second monostable vibrator connected to a second spline second N-channel Enhancement MOSFET pass transistor, and wherein the fifth Clk/Trig signal triggers the second spline second monostable vibrator to send a sixth Clk/Trig signal along a sixth Clk/Trig conductor and to activate the second spline second N-channel Enhancement MOSFET pass transistor connected to the second spline second electrode to transmit a second spline second electrode voltage sample along the second spline Vout conductor to the controller, and
   iii) wherein the sixth Clk/Trig conductor is connected to a second spline first monostable vibrator connected to a second spline first N-channel Enhancement MOSFET pass transistor, and wherein the sixth Clk/Trig signal triggers the second spline first monostable vibrator to activate the second spline first N-channel Enhancement MOSFET pass transistor connected to the second spline first electrode to transmit a second spline first electrode voltage sample along the second spline Vout conductor to the controller, and
   iv) wherein the second spline Gnd and Vsource conductors extend from the spline proximal anchor to at least the second spline first, second and third monostable vibrators.

5. The catheter system of claim 4, wherein the spline distal anchor comprises a terminal connector that electrically connects a distal end of the first spline to a distal end of the second spline.

6. The catheter system of claim 4, wherein transmitting the second spline first electrode voltage sample to the controller triggers the controller to initiate a second electrode sampling sequence by sending a first Clk/Trig signal along the first spline first Clk/Trig conductor to the first spline first monostable vibrator connected to the first spline first N-channel Enhancement MOSFET pass transistor to transmit a first spline first electrode voltage sample along the first spline Vout conductor to the controller.

7. The catheter system of claim 4, wherein there are at least three splines comprising the first spline, the second spline and a third spline, the third spline extending from the spline proximal anchor to the spline distal anchor, wherein the third spline comprises a third spline ground (Gnd) conductor, a third spline voltage-source (Vsource) conductor, and a third spline voltage-out (Vout) conductor, and wherein at least three electrodes are supported by the third spline, the at least three electrodes comprising a third spline first electrode located closest to the spline proximal anchor, a third spline second electrode, and a third spline third electrode located furthest from the spline proximal anchor, i) wherein the sixth Clk/Trig signal from the second spline second monostable vibrator also triggers the second spline first monostable vibrator to send a seventh Clk/Trig signal along a seventh Clk/Trig conductor connected to a third spline first monostable vibrator connected to a third spline first N-channel Enhancement MOSFET pass transistor, and wherein the seventh Clk/Trig signal triggers the third spline first monostable vibrator to send an eighth Clk/Trig signal along an eighth Clk/Trig conductor and to activate the third spline first N-channel Enhancement MOSFET pass transistor connected to the third spline first electrode to transmit a third spline first electrode voltage sample along the third spline Vout conductor to the controller, and ii) wherein the eighth Clk/Trig conductor is connected to a third spline second monostable vibrator connected to a third spline second N-channel Enhancement MOSFET pass transistor, and wherein the eighth Clk/Trig signal triggers the third spline second monostable vibrator to send a ninth Clk/Trig signal along a ninth Clk/Trig conductor and to activate the third spline second N-channel Enhancement MOSFET pass transistor connected to the third spline second electrode to transmit a third spline second electrode voltage sample along the third spline Vout conductor to the controller, and iii) wherein the ninth Clk/Trig conductor is connected to a third spline third monostable vibrator connected to a third spline third N-channel Enhancement MOSFET pass transistor, and wherein the ninth Clk/Trig signal triggers the third spline third monostable vibrator to activate the third spline third N-channel Enhancement MOSFET pass transistor connected to the third spline third electrode to transmit a third spline third electrode voltage sample along the third spline Vout conductor to the controller, and iv) wherein the third spline Gnd and Vsource conductors extend from the spline proximal anchor to at least the third spline first, second and third monostable vibrators.

8. The catheter system of claim 7, wherein the second spline third monostable vibrator is configured to send the fifth Clk/Trig signal along the fifth Clk/Trig conductor and to activate the second spline third N-channel Enhancement MOSFET pass transistor at a positive pulse of the fourth Clk/Trig signal, the second spline second monostable vibrator is configured to send the sixth Clk/Trig signal along the sixth Clk/Trig conductor and to activate the second spline second N-channel Enhancement MOSFET pass transistor at a positive pulse of the fifth Clk/Trig signal, and the second spline first monostable vibrator is configured to send the seventh Clk/Trig signal along the seventh Clk/Trig conductor and to activate the second spline first N-channel Enhancement MOSFET pass transistor at a positive pulse of the sixth Clk/Trig signal.

9. The catheter system of claim 4, wherein the first spline first monostable vibrator is configured to send the second Clk/Trig signal along the second Clk/Trig conductor and to activate the first spline first N-channel Enhancement MOSFET pass transistor at a positive pulse of the first Clk/Trig signal, the first spline second monostable vibrator is configured to send the third Clk/Trig signal along the third Clk/Trig conductor and to activate the first spline second N-channel Enhancement MOSFET pass transistor at a falling edge of a positive pulse of the second Clk/Trig signal, and the first spline third monostable vibrator is configured to send the fourth Clk/Trig signal along the fourth Clk/Trig conductor and to activate the first spline third N-channel Enhancement MOSFET pass transistor at a falling edge of a positive pulse of the third Clk/Trig signal.

10. The catheter system of claim 1, wherein the first spline first electrode comprises a first pair of first spline first electrodes that are configured to send a first pair of electrode voltage samples to the controller, the first spline second electrode comprises a second pair of first spline second electrodes that are configured to send a second pair of electrode voltage samples to the controller, and the first spline third electrode comprises a third pair of first spline third electrodes that are configured to send a third pair of electrode voltage samples to the controller, and wherein, with the first spline contacting cardiac tissue, the first pair of first spline first electrode voltage samples, the second pair of first spline second electrode voltage samples, and the third pair of first spline third electrode voltage samples are first, second and third bipolar Intracardiac Electrogram (EGM) voltage samples, respectively.

11. The catheter system of claim 10, wherein, with the first spline contacting cardiac tissue, the first pair of first spline first electrodes simultaneously send the first pair of electrode voltage samples to the controller, the second pair of first spline second electrodes simultaneously send the second pair of electrode voltage samples to the controller, and the third pair of first spline third electrodes simultaneously send the third pair of electrode voltage samples to the controller.

12. The catheter system of claim 1, wherein a system analog-to-digital (A/D) converter resides in the catheter, and wherein the system A/D converter is configured to convert the first spline first, second and third electrode voltage samples to respective first spline first, second and third digital electrode voltage samples.

13. The catheter system of claim 1, wherein a first analog-to-digital (A/D) converter connects from the first spline first electrode to the first spline first N-channel Enhancement MOSFET pass transistor connected to the first spline first monostable vibrator, a second A/D converter connects from the first spline second electrode to the first spline second N-channel Enhancement MOSFET pass transistor connected to the first spline second monostable vibrator, and a third A/D converter connects from the first spline third electrode to the first spline third N-channel Enhancement MOSFET pass transistor connected to the first spline third monostable vibrator.

14. The catheter system of claim 1, wherein the first spline first electrode, the first spline second electrode, and the first spline third electrode are individually first, second and third ring-shaped electrodes.

15. The catheter system of claim 14, wherein the first spline first monostable vibrator connected to the first spline first N-channel Enhancement MOSFET pass transistor are positioned inside the first spline first ring-shaped electrode, the first spline second monostable vibrator connected to the first spline second N-channel Enhancement MOSFET pass transistor are positioned inside the first spline second ring-shaped electrode, and the first spline third monostable vibrator connected to the first spline third N-channel Enhancement MOSFET pass transistor are positioned inside the first spline third ring-shaped electrode.

16. The catheter system of claim 1, wherein the first spline is a flex circuit comprising the first spline first electrode, the first spline second electrode and the first spline third electrode, and wherein the first spline first electrode is supported on a cylindrically-shaped first insulator, the first spline second electrode is supported on a cylindrically-shaped second insulator, and the first spline third electrode is supported on a cylindrically-shaped third insulator.

17. The catheter system of claim 1, wherein an input of the first spline first monostable vibrator is connected to the first spline first Clk/Trig conductor receiving the Clk/Trig signal from the controller, an input of the first spline second monostable vibrator is connected to an output of the first spline first monostable vibrator, and an input of the first spline third monostable vibrator is connected to an output of the first spline second monostable vibrator.

18. The catheter system of claim 1, wherein:
   i) the first spline first electrode is connected to a drain terminal of the first spline first N-Channel Enhancement-MOSFET pass transistor, and wherein an output of the first spline first monostable vibrator is connected to a gate of the first spline first N-Channel Enhancement-MOSFET pass transistor, and wherein the first spline Vout conductor is connected to a first source terminal of the first spline first N-Channel Enhancement-MOSFET pass transistor,
   ii) the first spline second electrode is connected to a drain terminal of the first spline second N-Channel Enhancement-MOSFET pass transistor, and wherein an output of the first spline second monostable vibrator is connected to a gate of the first spline second N-Channel Enhancement-MOSFET pass transistor, and wherein the first spline Vout conductor is connected to a second source terminal of the first spline second N-Channel Enhancement-MOSFET pass transistor, and
   iii) the first spline third electrode is connected to a drain terminal of the first spline third N-Channel Enhancement-MOSFET pass transistor, and wherein an output of the first spline third monostable vibrator is connected to a gate of the first spline third N-Channel Enhancement-MOSFET pass transistor, and wherein the first spline Vout conductor is connected to a third source terminal of the first spline third N-Channel Enhancement-MOSFET pass transistor.

19. The catheter system of claim 1, wherein:
   i) the first spline first electrode voltage sample is transmitted along the first spline Vout conductor connected to the first source terminal of the first spline first N-Channel Enhancement-MOSFET pass transistor,
   ii) the first spline second electrode voltage sample is transmitted along the first spline Vout conductor connected to the second source terminal of the first spline second N-Channel Enhancement-MOSFET pass transistor, and
   iii) the first spline third electrode voltage sample is transmitted along the first spline Vout conductor connected to the first spline third source terminal of the third N-Channel Enhancement-MOSFET pass transistor.

20. A catheter system, comprising:
   a) a controller;
   b) a flexible, elongate catheter extending from a catheter proximal connector to a catheter distal connector, the catheter proximal connector being electrically connectable to the controller;
   c) at least a first spline extending from a spline proximal anchor to a spline distal anchor, the spline proximal anchor being electrically connectable to the catheter distal connector, wherein the first spline comprises a first spline ground (Gnd) conductor, a first spline voltage-source (Vsource) conductor, and a first spline voltage-out (Vout) conductor, and wherein at least three electrodes are supported by the first spline, the at least three electrodes comprising a first spline first electrode, a first spline second electrode, and a first spline third electrode,
   d) wherein, with the catheter proximal connector electrically connected to the controller and with the spline proximal anchor electrically connected to the catheter distal connector, the controller is configured to initiate a first electrode sampling sequence along the first spline comprising a first spline first monostable vibrator connected to a first spline first N-channel Enhancement MOSFET pass transistor, by:
      i) sending a first clock/trigger (Clk/Trig) signal along a first spline first Clk/Trig conductor to trigger the first spline first monostable vibrator to send a second Clk/Trig signal along a second Clk/Trig conductor and to activate the first spline first N-channel Enhancement MOSFET pass transistor connected to the first spline first electrode to transmit a first spline first electrode voltage sample along the first spline Vout conductor to the controller, and
      ii) wherein the second Clk/Trig conductor is connected to a first spline second monostable vibrator connected to a first spline second N-channel Enhancement MOSFET pass transistor, and wherein the second Clk/Trig signal triggers the first spline second monostable vibrator to send a third Clk/Trig signal along a third Clk/Trig conductor and to activate the first spline second N-channel Enhancement MOSFET pass transistor connected to the first spline second electrode to transmit a first spline second electrode voltage sample along the first spline Vout conductor to the controller, and
      iii) wherein the third Clk/Trig conductor is connected to a first spline third monostable vibrator connected to a first spline third N-channel Enhancement MOSFET pass transistor, and wherein the third Clk/Trig signal triggers the first spline third monostable vibrator to activate the first spline third N-channel Enhancement MOSFET pass transistor connected to the first spline third electrode to transmit a first spline third electrode voltage sample along the first spline Vout conductor to the controller, and
      iv) wherein the first spline Gnd and Vsource conductors extend from the spline proximal anchor to at least the first spline first, second and third monostable vibrators.

21. The catheter system of claim 20, wherein with the at least first spline contacting cardiac tissue, the first spline first, second and third electrode voltage samples relate to respective unipolar Intracardiac Electrogram (EGM) voltage samples.

22. The catheter system of claim 20, wherein, transmitting the first spline third electrode voltage sample to the controller triggers the controller to initiate a second electrode sampling sequence by sending a first Clk/Trig signal along the first spline first Clk/Trig conductor to trigger the first spline first monostable vibrator to send a second Clk/Trig signal along the second Clk/Trig conductor and to activate the first spline first N-channel Enhancement MOSFET pass transistor to transmit a first spline first electrode voltage sample along the first spline Vout conductor to the controller.

23. The catheter system of claim 20, wherein there are at least two splines comprising the first spline and a second spline, the second spline extending from the spline proximal anchor to the spline distal anchor, and wherein the second spline comprises a second spline ground (Gnd) conductor, a second spline voltage-source (Vsource) conductor, and a second spline voltage-out (Vout) conductor, and wherein at least three electrodes are supported by the second spline, the at least three electrodes comprising a second spline first electrode, a second spline second electrode, and a second spline third electrode,
  i) wherein the third Clk/Trig signal from the first spline second monostable vibrator also triggers the first spline third monostable vibrator to send a fourth Clk/Trig signal along a fourth Clk/Trig conductor connected to the spline distal anchor and then to a fifth Clk/Trig conductor connected to a second spline first monostable vibrator connected to a second spline first N-channel Enhancement MOSFET pass transistor, and wherein the fourth Clk/Trig signal triggers the second spline first monostable vibrator to send a fifth Clk/Trig signal along a sixth Clk/Trig conductor and to activate the second spline first N-channel Enhancement MOSFET pass transistor connected to the second spline first electrode to transmit a second spline first electrode voltage sample along the second spline Vout conductor to the controller, and
  ii) wherein the sixth Clk/Trig conductor is connected to a second spline second monostable vibrator connected to a second spline second N-channel Enhancement MOSFET pass transistor, and wherein the fifth Clk/Trig signal triggers the second spline second monostable vibrator to send a sixth Clk/Trig signal along a seventh Clk/Trig conductor and to activate the second spline second N-channel Enhancement MOSFET pass transistor connected to the second spline second electrode to transmit a second spline second electrode voltage sample along the second spline Vout conductor to the controller, and
  iii) wherein the seventh Clk/Trig conductor is connected to a second spline third monostable vibrator connected to a second spline third N-channel Enhancement MOSFET pass transistor, and wherein the sixth Clk/Trig signal triggers the second spline third monostable vibrator to activate the second spline third N-channel Enhancement MOSFET pass transistor connected to the second spline third electrode to transmit a second spline third electrode voltage sample along the second spline Vout conductor to the controller, and
  iv) wherein the second spline Gnd and Vsource conductors extend from the spline proximal anchor to at least the second spline first, second and third monostable vibrators.

24. The catheter system of claim 23, wherein, with the spline proximal anchor electrically connected to the catheter distal connector, the first spline is electrically connected to the second spline in the spline proximal anchor.

25. The catheter system of claim 23, wherein transmitting the second spline third electrode voltage sample to the controller triggers the controller to initiate the second electrode sampling sequence by sending a first Clk/Trig signal along the first spline first Clk/Trig conductor extending from the spline proximal anchor to the first spline first monostable vibrator connected to the first spline first N-channel Enhancement MOSFET pass transistor to transmit a first spline first electrode voltage sample along the first spline Vout conductor to the controller.

26. The catheter system of claim 23, wherein the first spline first electrode comprises a first pair of first spline first electrodes that are configured to send a first pair of electrode voltage samples to the controller, the first spline second electrode comprises a second pair of first spline second electrodes that are configured to send a second pair of electrode voltage samples to the controller, and the first spline third electrode comprises a third pair of first spline third electrodes that are configured to send a third pair of electrode voltage samples to the controller, and wherein, with at least the first spline contacting cardiac tissue, the first pair of first spline first electrode voltage samples, the second pair of first spline second electrode voltage samples, and the third pair of first spline third electrode voltage samples are first, second and third bipolar Intracardiac Electrogram (EGM) voltage samples, respectively.

27. The catheter system of claim 26, wherein, with at least the first spline contacting cardiac tissue, the first pair of first spline first electrodes simultaneously send the first pair of electrode voltage samples to the controller, the second pair of first spline second electrodes simultaneously send the second pair of electrode voltage samples to the controller, and the third pair of first spline third electrodes simultaneously send the third pair of electrode voltage samples to the controller.

28. The catheter system of claim 23, wherein the fourth and fifth Clk/Trig conductors are either a unitary conductor or are separate conductors.

29. The catheter system of claim 20, wherein a system analog-to-digital (A/D) converter resides in the catheter, and wherein the system A/D converter is configured to convert the first spline first, second and third electrode voltage samples to respective first spline first, second and third digital electrode voltage samples.

30. The catheter system of claim 20, wherein a first analog-to-digital (A/D) converter connects from the first spline first electrode to the first spline first N-channel Enhancement MOSFET pass transistor connected to the first spline first monostable vibrator, a second A/D converter connects from the first spline second electrode to the first spline second N-channel Enhancement MOSFET pass transistor connected to the first spline second monostable vibrator, and a third A/D converter connects from the first spline third electrode to the first spline third N-channel Enhancement MOSFET pass transistor connected to the first spline third monostable vibrator.

31. The catheter system of claim 20, wherein the first spline first electrode, the first spline second electrode, and the first spline third electrode are individually first, second and third ring-shaped electrodes.

32. The catheter system of claim 31, wherein the first spline first monostable vibrator connected to the first spline first N-channel Enhancement MOSFET pass transistor are positioned inside the first spline first ring-shaped electrode, the first spline second monostable vibrator connected to the first spline second N-channel Enhancement MOSFET pass transistor are positioned inside the first spline second ring-shaped electrode, and the first spline third monostable vibrator connected to the first spline third N-channel Enhancement MOSFET pass transistor are positioned inside the first spline third ring-shaped electrode.

33. The catheter system of claim 20, wherein the first spline is a flex circuit comprising the first spline first electrode, the first spline second electrode and the first spline third electrode, and wherein the first spline first electrode is supported on a cylindrically-shaped first insulator, the first spline second electrode is supported on a cylindrically-shaped second insulator, and the first spline third electrode is supported on a cylindrically-shaped third insulator.

34. The catheter system of claim 14, wherein an input of the first spline first monostable vibrator is connected to the first spline first Clk/Trig conductor receiving the first Clk/Trig signal from the controller, an input of the first spline second monostable vibrator is connected to an output of the first spline first monostable vibrator, and an input of the first spline third monostable vibrator is connected to an output of the first spline second monostable vibrator.

35. The catheter system of claim 20, wherein:
   i) the first spline first electrode is connected to a drain terminal of the first spline first N-Channel Enhancement-MOSFET pass transistor, and wherein an output of the first spline first monostable vibrator is connected to a gate of the first spline first N-Channel Enhancement-MOSFET pass transistor, and wherein the first spline Vout conductor is connected to a first source terminal of the first spline first N-Channel Enhancement-MOSFET pass transistor,
   ii) the first spline second electrode is connected to a drain terminal of the first spline second N-Channel Enhancement-MOSFET pass transistor, and wherein an output of the first spline second monostable vibrator is connected to a gate of the first spline second N-Channel Enhancement-MOSFET pass transistor, and wherein the first spline Vout conductor is connected to a first spline second source terminal of the first spline second N-Channel Enhancement-MOSFET pass transistor, and
   iii) the first spline third electrode is connected to a drain terminal of the first spline third N-Channel Enhancement-MOSFET pass transistor, and wherein the output of the first spline third monostable vibrator is connected to a gate of the first spline third N-Channel Enhancement-MOSFET pass transistor, and wherein the first spline Vout conductor is connected to a first spline third source terminal of the first spline third N-Channel Enhancement-MOSFET pass transistor.

36. The catheter system of claim 35, wherein:
   i) the first spline first electrode voltage sample is transmitted along the first spline Vout conductor connected to the first spline first source terminal of the first spline first N-Channel Enhancement-MOSFET pass transistor,
   ii) the first spline second electrode voltage sample is transmitted along the first spline Vout conductor connected to the first spline second source terminal of the first spline second N-Channel Enhancement-MOSFET pass transistor, and
   iii) the first spline third electrode voltage sample is transmitted along the first spline Vout conductor connected to the first spline third source terminal of the third N-Channel Enhancement-MOSFET pass transistor.

37. A spline system that is detachably connectable to a catheter, the spline system comprising:
   a) a first spline extending from a spline proximal anchor to a spline distal anchor, the spline proximal anchor being electrically connectable to a catheter, the first spline comprising:
      i) a first spline ground (Gnd) conductor, a first spline voltage-source (Vsource) conductor, and a first spline voltage-out (Vout) conductor;
      ii) at least three electrodes comprising a first spline first electrode located closest to the spline proximal anchor, a first spline second electrode, and a first spline third electrode located furthest from the spline proximal anchor;
      iii) a first spline first monostable vibrator connected to a first spline first N-channel Enhancement MOSFET pass transistor, wherein the first spline first monostable vibrator is configured to receive a first clock trigger (Clk/Trig) signal from the controller to trigger the first spline first monostable vibrator to send a second Clk/Trig signal along a second Clk/Trig conductor and to activate the first spline first N-channel Enhancement MOSFET pass transistor connected to the first spline first electrode to transmit a first spline first electrode voltage sample along the first spline Vout conductor to the spline proximal anchor;
      iv) wherein the second Clk/Trig conductor is connected to a first spline second monostable vibrator connected to a first spline second N-channel Enhancement MOSFET pass transistor, and wherein the second Clk/Trig signal triggers the first spline second monostable vibrator to send a third Clk/Trig signal along a third Clk/Trig conductor and to activate the first spline second N-channel Enhancement MOSFET pass transistor connected to the first spline second electrode to transmit a first spline second electrode voltage sample along the first spline Vout conductor electrically connectable to the spline proximal anchor; and
      v) wherein the third Clk/Trig conductor is connected to a first spline third monostable vibrator connected to a first spline third N-channel Enhancement MOSFET pass transistor, and wherein the third Clk/Trig signal triggers the first spline third monostable vibrator to send a fourth Clk/Trig signal along a fourth Clk/Trig conductor and to activate the first spline third N-channel Enhancement MOSFET pass transistor connected to the first spline third electrode to transmit a first spline third electrode voltage sample along the first spline Vout conductor electrically connectable to the spline proximal anchor,
      vi) wherein the first spline Gnd and Vsource conductors extend from the spline proximal anchor to at least the first spline first, second and third monostable vibrators; and
   b) a second spline extending from the spline proximal anchor to the spline distal anchor, the second spline comprising:
      i) a second spline ground (Gnd) conductor, a second spline voltage-source (Vsource) conductor, and a second spline voltage-out (Vout) conductor;
      ii) at least three electrodes comprising a second spline first electrode located closest to the spline proximal anchor, a second spline second electrode, and a second spline third electrode located furthest from the spline proximal anchor;
      iii) a second spline third monostable vibrator connected to a second spline third N-channel Enhancement MOSFET pass transistor, wherein the fourth Clk/Trig signal triggers the first spline third monostable vibrator to send a fifth Clk/Trig signal along a fifth Clk/Trig conductor and to activate the second spline third N-channel Enhancement MOSFET pass transistor connected to the second spline third electrode to transmit a second spline third electrode voltage sample along the second spline Vout conductor to the spline proximal anchor, and iv) wherein the fifth Clk/Trig conductor is connected to a second spline second monostable vibrator connected to a second spline second N-channel Enhancement MOSFET pass transistor, and wherein the fifth Clk/Trig signal triggers the second spline second monostatic vibrator to send a sixth Clk/Trig signal along a sixth Clk/Trig conductor and to activate the second spline second N-channel Enhancement MOSFET pass transistor connected to the second spline second electrode to transmit a second spline second electrode voltage sample along the second spline Vout conductor to the spline proximal anchor, and v) wherein the sixth Clk/Trig conductor is connected to a second spline first monostable vibrator connected to a second spline first N-channel Enhancement MOSFET pass transistor, and wherein the sixth Clk/Trig signal triggers the second spline first monostatic vibrator to activate the second spline first N-channel Enhancement MOSFET pass transistor connected to the second spline first electrode to transmit a second spline first electrode voltage sample along the second spline Vout conductor to the spline proximal anchor, and vi) wherein the second spline Gnd and Vsource conductors extend from the spline proximal anchor to at least the second spline first, second and third monostable vibrators.

38. A spline system that is detachably connectable to a catheter, the spline system comprising:

a) a first spline extending from a spline proximal anchor to a spline distal anchor, the spline proximal anchor being electrically connectable to a catheter, the first spline comprising:

i) a first spline ground (Gnd) conductor, a first spline voltage-source (Vsource) conductor, and a first spline voltage-out (Vout) conductor;

ii) at least three electrodes comprising a first spline first electrode located closest to the spline proximal anchor, a first spline second electrode, and a first spline third electrode located furthest from the spline proximal anchor;

iii) a first spline first monostable vibrator connected to a first spline first N-channel Enhancement MOSFET pass transistor, wherein the first spline first monostable vibrator is configured to receive a first clock trigger (Clk/Trig) signal to trigger the first spline first monostable vibrator to send a second Clk/Trig signal along a second Clk/Trig conductor and to activate the first spline first N-channel Enhancement MOSFET pass transistor connected to the first spline first electrode to transmit a first spline first electrode voltage sample along the first spline Vout conductor to the spline proximal anchor;

iv) wherein the second Clk/Trig conductor is connected to a first spline second monostable vibrator connected to a first spline second N-channel Enhancement MOSFET pass transistor, and wherein the second Clk/Trig signal triggers the first spline second monostable vibrator to send a third Clk/Trig signal along a third Clk/Trig conductor and to activate the first spline second N-channel Enhancement MOSFET pass transistor connected to the first spline second electrode to transmit a first spline second electrode voltage sample along the first spline Vout conductor to the spline proximal anchor; and v) wherein the third Clk/Trig conductor is connected to a first spline third monostable vibrator connected to a first spline third N-channel Enhancement MOSFET pass transistor, and wherein the third Clk/Trig signal triggers the first spline third monostable vibrator to activate the first spline third N-channel Enhancement MOSFET pass transistor connected to the first spline third electrode to transmit a first spline third electrode voltage sample along the first spline Vout conductor to the spline proximal anchor, and vi) wherein the first spline Gnd and Vsource conductors extend from the spline proximal anchor to at least the first spline first, second and third monostable vibrators.

39. The spline system of claim 38, wherein a second spline extends from the spline proximal anchor to the spline distal anchor, the second spline comprising:

i) a second spline ground (Gnd) conductor, a second spline voltage-source (Vsource) conductor, and a second spline voltage-out (Vout) conductor;

ii) at least three electrodes comprising a second spline first electrode located closest to the spline proximal anchor, a second spline second electrode, and a second spline third electrode located furthest from the spline proximal anchor;

iii) a second spline first monostable vibrator connected to a second spline first N-channel Enhancement MOSFET pass transistor, wherein the third Clk/Trig signal from the first spline second monostable vibrator also triggers the first spline third monostable vibrator to send a fourth Clk/Trig signal along a fourth Clk/Trig conductor connected to the second spline first monostable vibrator to trigger the second spline first monostable vibrator to send a fifth Clk/Trig signal along a fifth Clk/Trig conductor and to activate the second spline first N-channel Enhancement MOSFET pass transistor connected to the second spline first electrode to transmit a second spline first electrode voltage sample along the second spline Vout conductor to the spline proximal anchor;

iv) wherein the fifth Clk/Trig conductor is connected to a second spline second monostable vibrator connected to a second spline second N-channel Enhancement MOSFET pass transistor, and wherein the fifth Clk/Trig signal triggers the second spline second monostable vibrator to send a sixth Clk/Trig signal along a sixth Clk/Trig conductor and to activate the second spline second N-channel Enhancement MOSFET pass transistor connected to the second spline second electrode to transmit a second spline second electrode voltage sample along the second spline Vout conductor to the spline proximal anchor; and vi) wherein the sixth Clk/Trig conductor is connected to a second spline third monostable vibrator connected to a second spline third N-channel Enhancement MOSFET pass transistor, and wherein the sixth Clk/Trig signal triggers the second spline third monostable vibrator to activate the second spline third N-channel Enhancement MOSFET pass transistor connected to the second spline third electrode to transmit a second spline third electrode voltage sample along the second spline Vout conductor to the spline proximal anchor, vii) wherein the second spline Gnd and Vsource conductors extend from the spline proximal anchor to at least the second spline first, second and third monostable vibrators.

\* \* \* \* \*